(12) United States Patent
Takahashi

(10) Patent No.: US 8,409,081 B2
(45) Date of Patent: Apr. 2, 2013

(54) ILLUMINATION LIGHT APPLICATION STRUCTURE AND ENDOSCOPE PROVIDED WITH THE SAME

(75) Inventor: Susumu Takahashi, Iruma (JP)

(73) Assignee: Olympus Medical Systems Corp., Tokyo (JP)

( * ) Notice: Subject to any disclaimer, the term of this patent is extended or adjusted under 35 U.S.C. 154(b) by 1381 days.

(21) Appl. No.: 12/148,716

(22) Filed: Apr. 21, 2008

(65) Prior Publication Data

US 2008/0269563 A1 Oct. 30, 2008

(30) Foreign Application Priority Data

Apr. 27, 2007 (JP) ................................. 2007-119232
Apr. 8, 2008 (JP) ................................. 2008-100540

(51) Int. Cl.
*A61B 1/06* (2006.01)
*G02B 6/06* (2006.01)

(52) U.S. Cl. ........................................ 600/177; 385/117

(58) Field of Classification Search .......... 385/116–117; 600/138, 177, 178, 179, 182, 160, 342–343
See application file for complete search history.

(56) References Cited

U.S. PATENT DOCUMENTS

| | | | | |
|---|---|---|---|---|
| 5,689,602 A * | 11/1997 | Arai | ............................... | 385/119 |
| 5,751,417 A * | 5/1998 | Uhl | ................................ | 356/318 |
| 6,063,024 A * | 5/2000 | Yamamoto | ..................... | 600/160 |
| 6,108,090 A * | 8/2000 | Ishihara | ......................... | 356/601 |
| 6,122,098 A * | 9/2000 | Kask et al. | ..................... | 359/368 |
| 6,478,732 B2 * | 11/2002 | Adachi | ......................... | 600/178 |
| 6,510,001 B1 * | 1/2003 | Engelhardt et al. | ........... | 359/385 |
| 6,921,920 B2 * | 7/2005 | Kazakevich | ..................... | 257/81 |
| 7,252,634 B2 * | 8/2007 | Mizumo | ......................... | 600/160 |
| 7,267,647 B2 * | 9/2007 | Okada et al. | .................. | 600/166 |
| 7,422,356 B2 * | 9/2008 | Hama et al. | ................... | 362/574 |
| 2002/0143239 A1 * | 10/2002 | Henzler | ......................... | 600/179 |
| 2007/0213592 A1 * | 9/2007 | Yamada | ......................... | 600/178 |

FOREIGN PATENT DOCUMENTS

| | | |
|---|---|---|
| JP | 04-244130 | 9/1992 |
| JP | 10-216085 | 8/1998 |

* cited by examiner

*Primary Examiner* — Philip R Smith
(74) *Attorney, Agent, or Firm* — Kenyon & Kenyon LLP

(57) ABSTRACT

An illumination light application structure provided for irradiating an observation object with illumination light in an observation optical apparatus provided with an objective optical system inside a lens barrel whose top is configured into a slender shape, includes a wavelength converting element located in the proximity of a position of an entrance pupil of the objective optical system; a light source emitting light whose wavelength is converted by the wavelength converting element; and an irradiation device irradiating the wavelength converting element with the light emitted from the light source through the objective optical system.

61 Claims, 18 Drawing Sheets

FIG.6
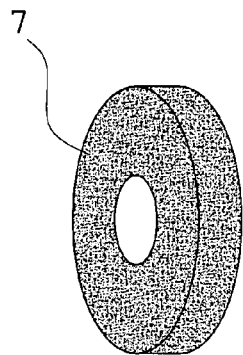
FIG.7
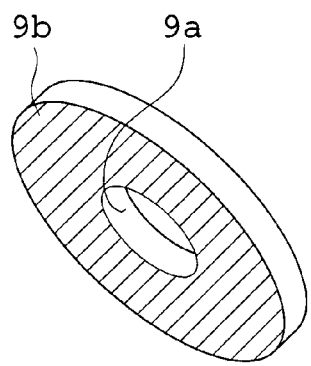
FIG.8A                    FIG.8B
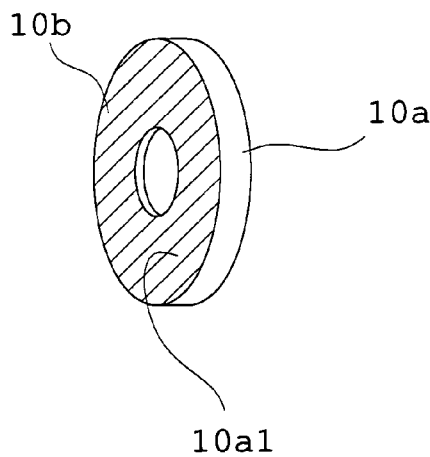    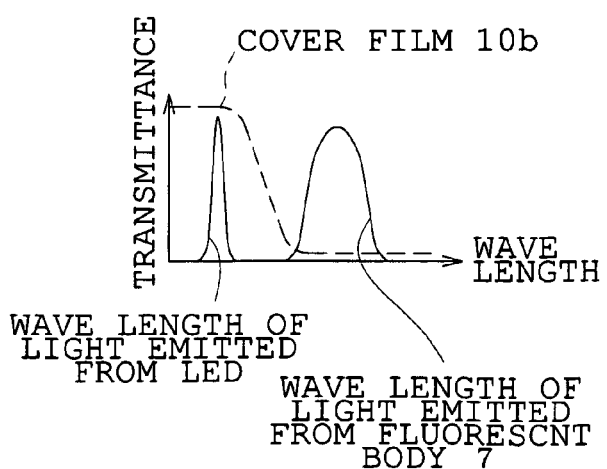

ILLUMINATION LIGHT APPLICATION STRUCTURE AND ENDOSCOPE PROVIDED WITH THE SAME

This application claims benefits of Japanese Patent Application No. 2007-119232 filed in Japan on Apr. 27, 2007, and No. 2008-100540 filed in Japan on Apr. 8, 2008, the contents of which are incorporated herein by reference.

BACKGROUND OF THE INVENTION

1. Field of the Invention

This invention relates to an illumination light application structure for irradiating an observation object with illumination light in an observation optical apparatus provided with an objective lens inside a lens barrel whose top is configured into a slender shape, and to an endoscope provided with this illumination light application structure.

2. Description of Related Art

Endoscopes have been used for observations of parts in which observations from the exterior are difficult, such as internal therapies and/or diagnoses of patients in a medical field and internal inspections of holes provided in products in an industrial field.

In general, the endoscope has an objective optical system and an image transmitting optical system such as a relay lens (in the case of a rigid scope) and an image guide fiber (in the case of a flexible scope) inside a tubular insertion section of tiny diameter at the distal end. The endoscope is thus constructed so that light passing through these optical systems from an observation object is observed as an observation image through an ocular optical system and an imaging optical system. A video endoscope is designed to house the objective optical system and an image sensor, such as a CCD, in the distal end.

In the endoscope, an illumination means for illuminating the observation object observed through the objective optical system is placed on an optical path different from that of the objective optical system. The structures of the illumination means in such endoscopes are set forth, for example, in Japanese Patent Kokai Nos. Hei 10-216085 and Hei 4-244130. The illumination means of the endoscope set forth in Kokai No. 10-216085, for example, as shown in FIG. 1, is constructed so that, at a distal end 50 of the endoscope, a plurality of LEDs 52a and 52b are arranged around or on the side of an observation system 51 and the observation object is irradiated with illumination light from the plurality of LEDs 52a and 52b. On the other hand, the illumination means of the endoscope set forth in Kokai No. 4-244130, for example, as shown in FIG. 2, is constructed so that a light guide 62 is provided in an annular shape around an observation system 61 at a distal end 60 of the endoscope.

SUMMARY OF THE INVENTION

The illumination light application structure according to the present invention, provided for irradiating an observation object with illumination light in an observation optical apparatus provided with an objective optical system inside a lens barrel whose top is configured into a slender shape, comprises a wavelength converting element located in the proximity of the position of an entrance pupil of the objective optical system; a light source emitting light whose wavelength is converted by the wavelength converting element; and an irradiation means irradiating the wavelength converting element with the light emitted from the light source through the objective optical system.

The illumination light application structure according to the present invention, provided for irradiating an observation object with illumination light in an observation optical apparatus provided with an objective optical system inside a lens barrel whose top is configured into a slender shape, comprises a fluorescent body located in the proximity of the position of an entrance pupil of the objective optical system; a light source emitting light for exiting the fluorescent body; and an irradiation means irradiating the fluorescent body with the light emitted from the light source through the objective optical system.

The illumination light application structure according to the present invention, provided for irradiating an observation object with illumination light in an observation optical apparatus provided with an objective optical system inside a lens barrel whose top is configured into a slender shape, comprises an annular fluorescent body located in the proximity of the position of an entrance pupil of the objective optical system, having a size that its inside diameter is larger than the diameter of the entrance pupil of the objective optical system and its outside diameter is practically identical with the diameter of a lens of the largest diameter in the objective optical system; a light source emitting light for exciting the fluorescent body; and an irradiation means irradiating the fluorescent body with the light emitted from the light source through the objective optical system.

The illumination light application structure according to the present invention, provided for irradiating an observation object with illumination light in an observation optical apparatus provided with an objective optical system inside a lens barrel whose top is configured into a slender shape, comprises a light source; and an irradiation means irradiating an annular area having a size that its inside diameter is larger than the diameter of an entrance pupil of the objective optical system and its outside diameter is practically identical with the diameter of a lens of the largest diameter in the objective optical system, with light emitted from the light source through the objective optical system, in the proximity of the position of the entrance pupil of the objective optical system.

The illumination light application structure according to the present invention, provided for irradiating an observation object with illumination light in an observation optical apparatus provided with an objective optical system inside a lens barrel whose top is configured into a slender shape, comprises an annular scattering body located in the proximity of the position of an entrance pupil of the objective optical system, having a size its inside diameter is larger than the diameter of the entrance pupil of the objective optical system and its outside diameter is practically identical with the diameter of a lens of the largest diameter in the objective optical system; a light source; and an irradiation means irradiating the scattering body with light emitted from the light source through the objective optical system.

In the illumination light application structure of the present invention, it is desirable that the irradiation means is constructed with a reflecting mirror obliquely placed in the proximity of the position of a pupil conjugate with the entrance pupil of the objective optical system, including an opening having a diameter practically identical with that of the pupil conjugate with the entrance pupil of the objective optical system in a state where the reflecting mirror is obliquely placed and a reflecting surface reflecting the light emitted from the light source toward the objective optical system side, provided on the periphery of the opening.

In the illumination light application structure of the present invention, it is desirable that the irradiation means is provided with a reflecting mirror obliquely placed in the proximity of the position of a pupil conjugate with the entrance pupil of the objective optical system, including a reflecting surface having a diameter practically identical with that of the pupil conjugate with the entrance pupil of the objective optical system in a state where the reflecting mirror is obliquely placed and is constructed so that the fluorescent body is irradiated through the objective optical system with light passing through the periphery of the reflecting mirror, of the light emitted from the light source.

In the illumination light application structure of the present invention, it is desirable that the irradiation means is provided with a reflecting mirror obliquely placed in the proximity of the position of a pupil conjugate with the entrance pupil of the objective optical system, including a reflecting surface having a diameter practically identical with that of the pupil conjugate with the entrance pupil of the objective optical system in a state where the reflecting mirror is obliquely placed and is constructed so that the annular area is irradiated with light passing through the periphery of the reflecting mirror through the objective optical system, of the light emitted from the light source.

In the illumination light application structure of the present invention, it is desirable that the irradiation means is provided with a reflecting mirror obliquely placed in the proximity of the position of a pupil conjugate with the entrance pupil of the objective optical system, including a reflecting surface having a diameter practically identical with that of the pupil conjugate with the entrance pupil of the objective optical system in a state where the reflecting mirror is obliquely placed and is constructed so that the scattering body is irradiated with light passing through the periphery of the reflecting mirror, of the light emitted from the light source, through the objective optical system In the illumination light application structure of the present invention, it is desirable that the irradiation means is constructed so that a plurality of light sources are annularly arranged with respect to the optical axis of the objective optical system and individual light emitted from the plurality of light sources passes through the periphery of the pupil conjugate with the entrance pupil of the objective optical system.

In the illumination light application structure of the present invention, it is desirable that the irradiation means includes a half mirror obliquely placed in the proximity of the position of the pupil conjugate with the entrance pupil of the objective optical system so as to reflect the light emitted from the light source toward the objective optical system side and a barrier filter having a property of blocking the light emitted from the light source, placed on the image side of the half mirror.

In the illumination light application structure of the present invention, it is desirable that the irradiation means is constructed with a wavelength selective member having properties of reflecting the light emitted from the light source and transmitting light of remaining wavelengths and obliquely placed in the proximity of the position of the pupil conjugate with the entrance pupil of the objective optical system so as to reflect the light from the light source toward the objective optical system side.

In the illumination light application structure of the present invention, it is desirable that a fluorescence cutoff filter having properties of transmitting excitation light and blocking fluorescent light emanating from the fluorescent body is placed on the image side of the fluorescent body.

In the illumination light application structure of the present invention, it is desirable that a light-blocking member is provided inside an opening of the fluorescent body.

In the illumination light application structure of the present invention, it is desirable that a light-blocking member is provided inside openings of the fluorescent body and the fluorescence cutoff filter.

In the illumination light application structure of the present invention, it is desirable that a light-blocking member is provided inside an opening of the fluorescent body and in the proximity of an opening of the fluorescence cutoff filter.

In the illumination light application structure of the present invention, it is desirable that a cylindrical transparent member is provided inside the opening of the fluorescent body.

In the illumination light application structure of the present invention, it is desirable that a cylindrical transparent member is provided inside the openings of the fluorescent body and the fluorescence cutoff filter.

In the illumination light application structure of the present invention, it is desirable that an image transmitting optical system including one of a relay lens, an image fiber, and a SELFOC lens is provided on the image side of the objective optical system.

In the illumination light application structure of the present invention, it is desirable that the image transmitting optical system is constructed with the SELFOC lens and the irradiation means includes an illumination optical system having an optical axis inclined with respect to the optical axis of the SELFOC lens so that excitation light emitted from the light source is obliquely incident on the entrance surface of the SELFOC lens.

In the illumination light application structure of the present invention, it is desirable that the irradiation means includes chromatic aberration producing means placed on an optical path between the fluorescent body and the light source so that the fluorescent body is irradiated with excitation light through an optical path different from those of light of wavelengths other than the excitation light due to a color error action and the light source placed to lie around the objective optical system.

In the illumination light application structure of the present invention, it is desirable that the irradiation means includes chromatic aberration producing means placed on an optical path between the scattering body and the light source so that the scattering body is irradiated with light of preset wavelength through an optical path different from those of light of wavelengths other than the light of the preset wavelength due to a color error action and the light source placed to lie around the objective optical system.

In the illumination light application structure of the present invention, it is desirable that the chromatic aberration producing means includes a cemented lens or a diffraction grating.

In the illumination light application structure of the present invention, it is desirable to further comprise a fluorescence cutoff filter configured into a size that is smaller in inside diameter than the fluorescent body and is practically identical in outside diameter with the fluorescent body in the proximity of the position of the entrance pupil of the objective optical system and having properties of transmitting excitation light and blocking fluorescent light emanating from the fluorescent body; a transparent member configured into an annular shape that has inside and outside diameters practically identical in size with the fluorescent body, provided between the fluorescent body and the fluorescence cutoff filter; and a concave lens and a convex lens arranged in this order from the object side inside the transparent member.

In the illumination light application structure of the present invention, it is desirable that the observation optical apparatus is an endoscope.

In the illumination light application structure of the present invention, it is desirable that the light source is an LD or LED.

In the illumination light application structure of the present invention, it is desirable that the image transmitting optical system is constructed with a SELFOC lens and the SELFOC lens is provided with a low-refractive-index cladding layer on its periphery.

The endoscope according to the present invention is provided with the illumination light application structure in any aspect of the present invention.

According to the present invention, the illumination light application structure and the endoscope using this structure in which the diameter of the distal end can be made extremely tiny without causing halation and distortion asymmetrical with respect to the observation image.

These and other features and advantages of the present invention will become apparent from the following detailed description of the preferred embodiments when taken in conjunction with the accompanying drawings.

BRIEF DESCRIPTION OF THE DRAWINGS

FIG. 6 is an explanatory view showing an annular fluorescent body used as a wavelength converting element in the illumination light application structure of the endoscope of FIG. 3A.

FIG. 7 is an explanatory view showing one example of the irradiation means in the illumination light application structure of the endoscope of FIG. 3A.

FIGS. 8A and 8B are explanatory views of the fluorescence cutoff filter in the illumination light application structure of the endoscope of FIG. 3A, which are a perspective view showing the appearance and a graph showing the transmission characteristics of the fluorescence cutoff filter, respectively.

DETAILED DESCRIPTION OF THE PREFERRED EMBODIMENTS

First Embodiment

Figure 1:
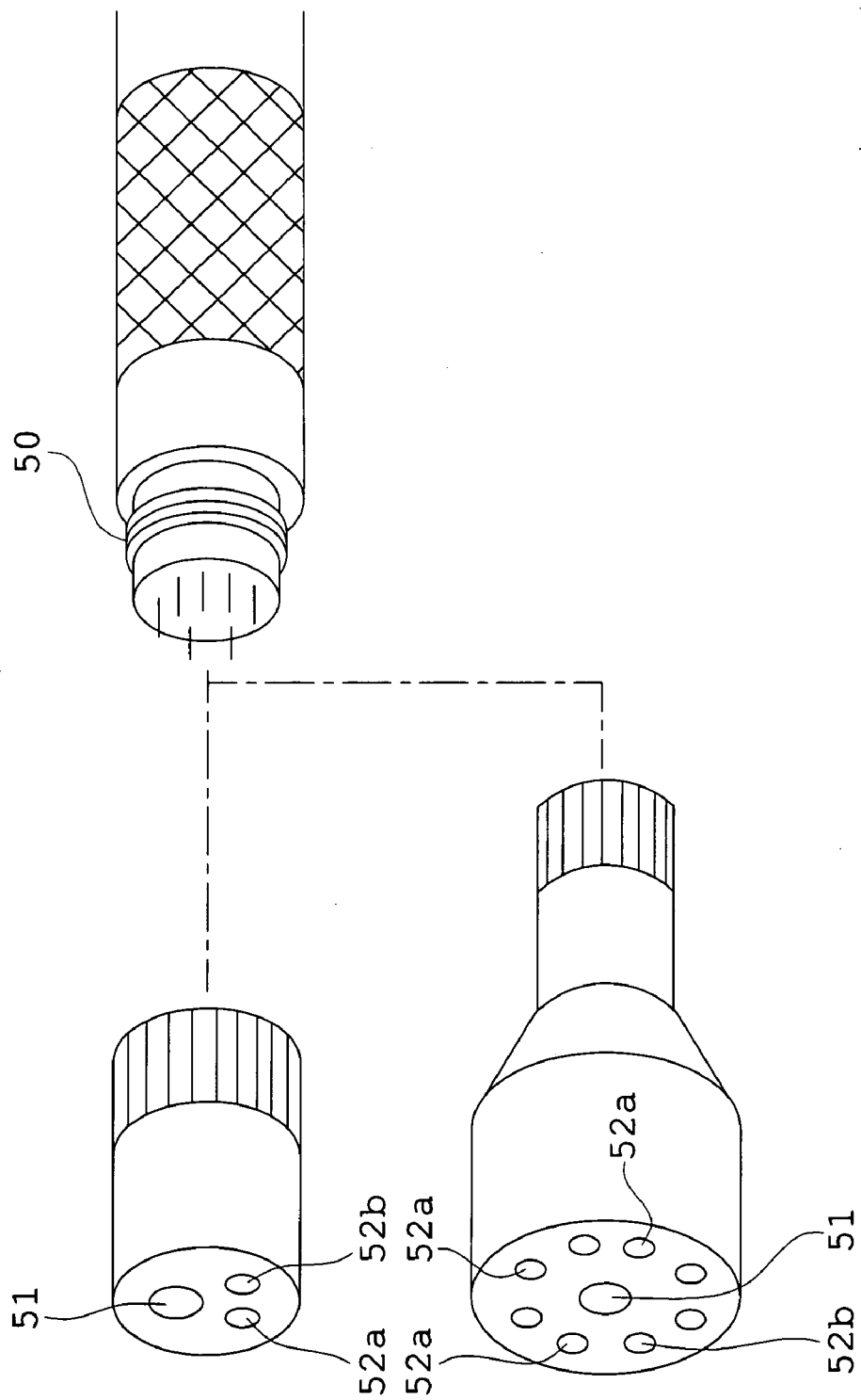
FIG. 1 is an explanatory view showing one structural example of an illumination means of a conventional endoscope.
Figure 2:
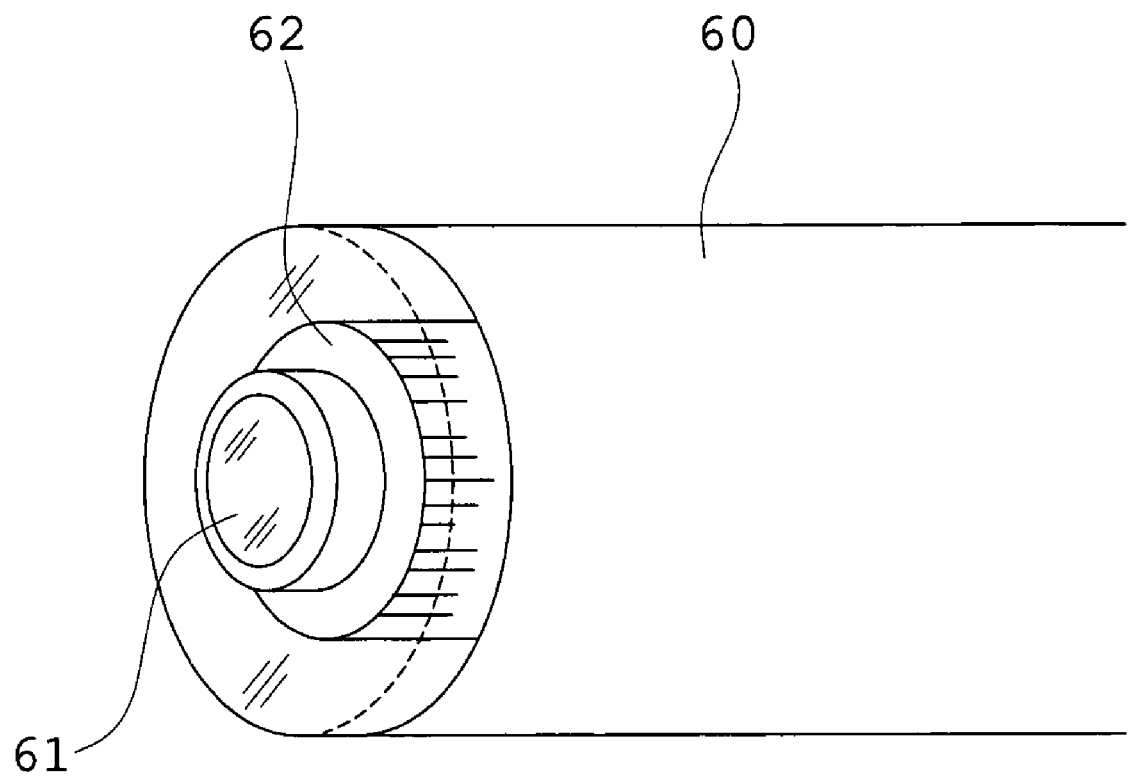
FIG. 2 is an explanatory view showing another structural example of the illumination means of the conventional endoscope.
Figure 3A:
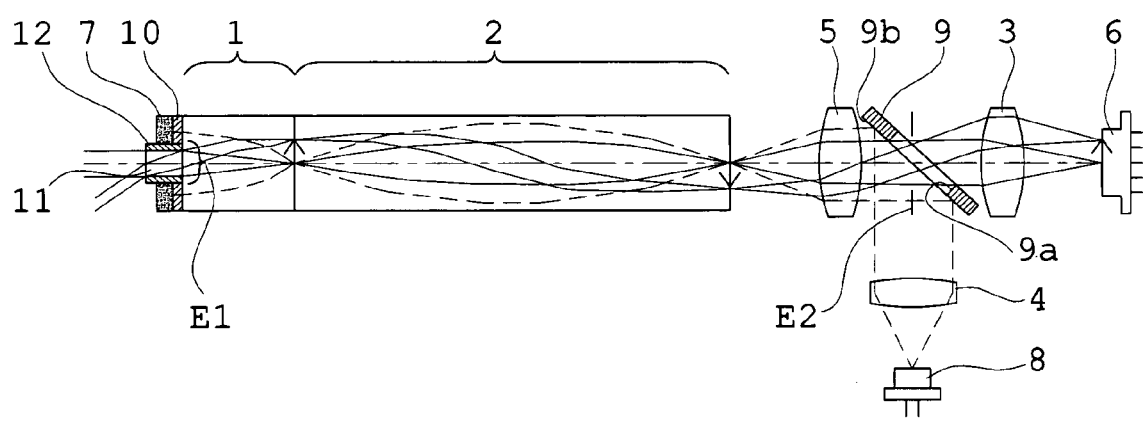
FIGS. 3A and 3B are explanatory views of an endoscope provided with the illumination light application structure according to a first embodiment in the present invention, showing a schematic optical arrangement of the endoscope and the appearance, respectively.
Figure 3B:
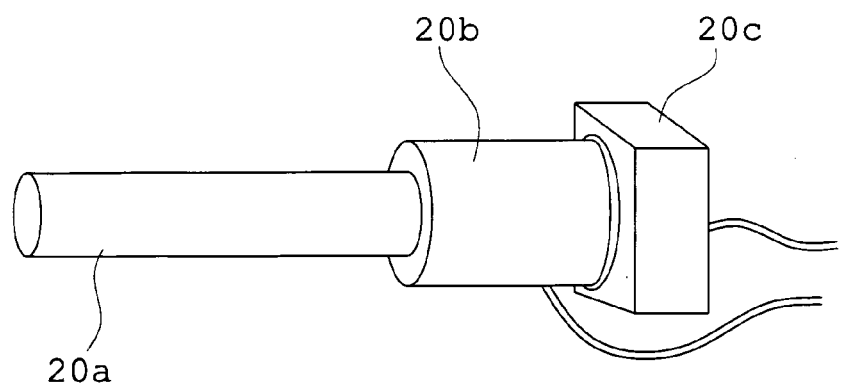
Figure 4:
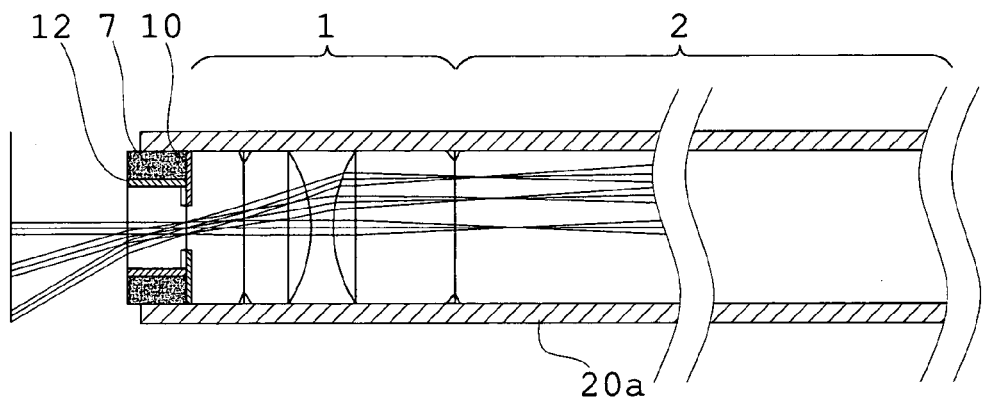
FIG. 4 is an enlarged explanatory view showing a modified example of the distal end in the illumination light application structure of the endoscope in FIG. 3A.
Figures 5A, 5B:
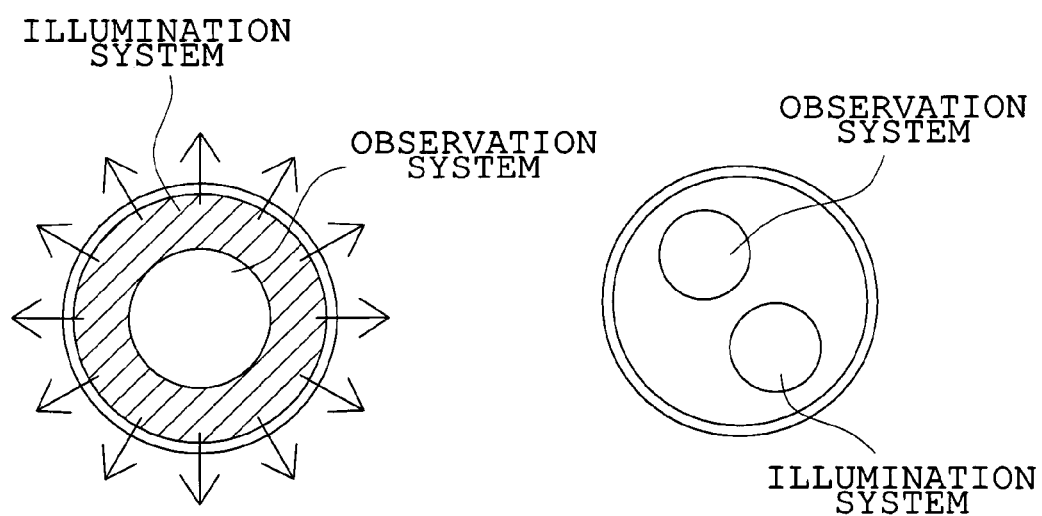
FIGS. 5A and 5B are explanatory views showing the distal end in the illumination light application structure of the endoscope of FIG. 3A and the distal end in the case where the distal end of the endoscope is configured into a tiny diameter to the same extent as in the first embodiment using the prior art, respectively, looking from the object side.
Figure 9:
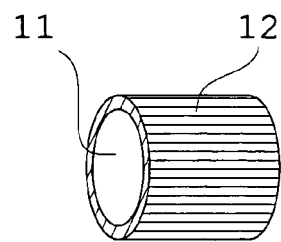
FIG. 9 is an explanatory view showing a cylindrical transparent member in the illumination light application structure of the endoscope of FIG. 3A.
Figure 10:
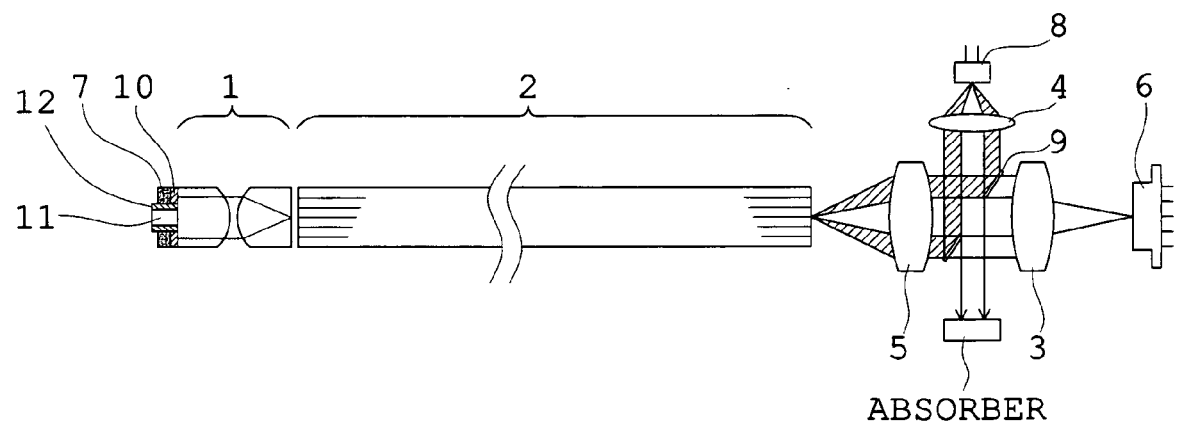
FIG. 10 is an explanatory view showing schematically an optical arrangement in the case where another image transmitting optical system is used in the illumination light application structure of the endoscope of FIG. 3A.

FIGS. 3A and 3B are explanatory views of an endoscope provided with the illumination light application structure according to a first embodiment in the present invention, showing a schematic optical arrangement of the endoscope and the appearance, respectively. FIG. 4 is an enlarged explanatory view showing a modified example of the distal end in the illumination light application structure of the endoscope in FIG. 3A. FIGS. 5A and 5B are explanatory views showing the distal end in the illumination light application structure of the endoscope of FIG. 3A and the distal end in the case where the distal end of the endoscope is configured into a tiny diameter to the same extent as in the first embodiment using the prior art, respectively, looking from the object side. FIG. 6 is an explanatory view showing an annular fluorescent body used as a wavelength converting element in the illumination light application structure of the endoscope of FIG. 3A. FIG. 7 is an explanatory view showing one example of the irradiation means in the illumination light application structure of the endoscope of FIG. 3A. FIGS. 8A and 8B are explanatory views of the fluorescence cutoff filter in the illumination light application structure of the endoscope of FIG. 3A, which are a perspective view showing the appearance and a graph showing the transmission characteristics of the fluorescence cutoff filter, respectively. FIG. 9 is an explanatory view showing a cylindrical transparent member in the illumination light application structure of the endoscope of FIG. 3A. FIG. 10 is an explanatory view showing schematically an optical arrangement in the case where another image transmitting optical system is used in the illumination light application structure of the endoscope of FIG. 3A.

The endoscope of the first embodiment, as shown in FIG. 3A, has an objective optical system 1, an image transmitting optical system 2, imaging optical systems 3 and 5, and an illumination optical system 4. The objective optical system 1 and the image transmitting optical system 2 are provided inside a lens barrel top section 20a configured into a slender shape. Each of the objective optical system 1 and the image transmitting optical system 2 is constructed with a SELFOC lens. In FIGS. 3A and 3B, reference numeral 6 denotes an image sensor such as a CCD, 20b denotes a housing section in which the illumination optical system 4 and the imaging optical systems 3 and 5 are incorporated, and 20c denotes a housing section in which the image sensor 6 is incorporated.

The endoscope of the first embodiment further has, as the illumination light application structure, an annular fluorescent body 7 for a wavelength converting element (refer to FIG. 6), a light source 8 emitting excitation light, an irradiation means 9, an annular fluorescence cutoff filter 10, and a cylindrical transparent member 11. The fluorescent body 7 is configured into an annular shape in which its inside diameter is larger than the diameter of an entrance pupil E1 of the objective optical system 1 and its outside diameter is practically identical with the diameter of a lens having the largest diameter in the objective optical system 1. The fluorescent body 7 is located in the proximity of the position of the entrance pupil E1 of the objective optical system 1. The light source 8 uses an LED or LD to emit light of a preset wavelength exciting the fluorescent body 7.

The irradiation means 9 is constructed with an annular reflecting mirror such as that shown in FIG. 7. The annular reflecting mirror is obliquely placed in the proximity of the position of a pupil E2 conjugate with the entrance pupil E1 of the objective optical system 1 and includes an opening 9a having the diameter practically identical with the diameter of the pupil E2 conjugate with the entrance pupil E1 of the objective optical system in a state where the reflecting mirror is obliquely placed and a reflecting surface 9b reflecting the light emitted from the light source 8 toward the objective-optical-system-1 side, provided on the periphery of the opening 9a.

The fluorescence cutoff filter 10 is interposed between the fluorescent body 7 and objective optical system 1. The fluorescence cutoff filter 10 is constructed so that one surface 10a1 of an annular transparent member 10a, such as that shown in FIG. 8A, configured into a size that its inside diameter is larger than the diameter of the entrance pupil E1 of the objective optical system 1 and is smaller than the inside diameter of the fluorescent body 7 and its outside diameter is practically identical with that of the annular fluorescent body 7 is coated with a cover film 10b, such as that shown in FIG. 8B, having properties of transmitting the excitation light and blocking fluorescent light emanating from the fluorescent body 7.

The cylindrical transparent member 11 is configured into a diameter of such a size that it can be fitted into the openings of the fluorescent body 7 and fluorescence cutoff filter 10. Moreover, in the transparent member 11, its periphery is covered with a light-blocking member 12. In a state where the transparent member 11 is fitted into the openings the fluorescent body 7 and the fluorescence cutoff filter 10, the light-blocking member 12 is such as to cover the surfaces of the openings of the fluorescent body 7 and the fluorescence cutoff filter 10.

In the endoscope provided with the illumination light application structure of the first embodiment constructed as mentioned above, light emitted from the light source 8 is incident on the reflecting mirror 9 as the irradiation means through the illumination optical system 4. Of a light beam incident on the reflecting mirror 9, light entering the opening 9a passes therethrough as it is. This transmitted light can be absorbed by the proper placement of a light-absorbing member, not shown in the figure. On the other hand, light incident on the reflecting surface 9b is reflected toward the objective-optical-system-1 side and enters the objective optical system 1, as an annular light beam, through the imaging optical system 5 and the image transmitting optical system 2. The light entering the objective optical system 1 passes through the outside position of the entrance pupil E1 at the position of the entrance pupil E1 of the objective optical system 1 and is transmitted through the fluorescence cutoff filter 10 to enter the fluorescent body 7. Whereby, the fluorescent body 7 is excited to emit fluorescent light. Of the fluorescent light emitted from the fluorescent body 7, fluorescent light directed toward the object side is used as illumination light for illumination of the observation object. Also, fluorescent light directed toward the image side is reflected by the cover film 10b of the fluorescence cutoff filter 10, so that this light as well is used for illumination. Fluorescent light directed toward the optical axis side of the objective optical system 1 is blocked by the light-blocking member 12. Light from an illuminated observation object is incident on the cylindrical transparent member 11 and is imaged on the image pickup surface of the image sensor 6 through the objective optical system 1, the image transmitting optical system 2, and the imaging optical systems 5 and 3.

In the illumination light application structure of the first embodiment, as discussed above, the annular fluorescent body 7 configured into a size that its inside diameter is larger than the diameter of the entrance pupil E1 of the objective optical system 1 and its outside diameter is practically identical with the largest diameter of the objective optical system 1 is provided in the proximity of the position of the entrance pupil E1 of the objective optical system 1, and the fluorescent light emanating from the fluorescent body 7 in such a way that the fluorescent body 7 is irradiated with the excitation light through the irradiation means 9 is used as the illumination light. Specifically, in the illumination light application structure of the first embodiment, an observation system and an illumination system are made coaxial in respect of the objective optical system and the image transmitting optical system and an outside region unnecessary for the observation at the top of the observation system provided with the objective optical system 1 is used as the optical path of the illumination system. According to the illumination light application structure of the first embodiment, therefore, there is no need to provide the optical path for the illumination system around the objective optical system 1, and the optical apparatus, such as the endoscope, in which the distal end is made to have a tiny diameter to the extent impossible for the prior art described in Kokai Nos. Hei 10-216085 and Hei 4-244130, can be realized. Moreover, since it is not necessary that an illumination system optical member, such as a light guide, is eccentrically placed around the objective optical system, the occurrence of halation in the observation system caused by the problem that only one direction is brightly illuminated can be prevented. In addition, the observation system is placed at the center inside the insertion section of the distal end, and thus the occurrence of asymmetrical distortion of the observation image can also be prevented.

In the illumination light application structure of the first embodiment, the irradiation means 9 is constructed with the annular reflecting mirror which includes an opening 9a having the diameter practically identical with the diameter of the pupil E2 conjugate with the entrance pupil E1 of the objective optical system 1 in a state where the reflecting mirror is obliquely placed and a reflecting surface 9b reflecting the light emitted from the light source 8 toward the objective-optical-system-1 side, provided on the periphery of the opening 9a, and which is obliquely placed in the proximity of the position of the pupil E2 conjugate with the entrance pupil E1 of the objective optical system 1. Hence, the excitation light emitted form the light source 8 can be made incident on the fluorescent body 7 in such a way that the excitation light does not enter the entrance pupil E1 of the objective optical system 1 as far as possible. An observation light beam from the observation object is such that light passing through the entrance pupil E1 of the objective optical system 1 goes through the opening 9a and is imaged on the image pickup surface of the image sensor 6 through the imaging optical system 3. Even though other unwanted light is produced, the light is reflected by the reflecting surface 9b and thereby the incidence of the light on the imaging optical system 3 can be prevented. Consequently, even when the optical path of the illumination system is provided in the objective optical system 1, the observation object can be illuminated without obstructing the observation in the observation system.

According to the illumination light application structure of the first embodiment, the fluorescence cutoff filter 10 in which the one surface 10a1 of the transparent member 10a configured into an annular shape of a size that its inside diameter is larger than the diameter of the entrance pupil E1 of the objective optical system 1 and is smaller than the inside diameter of the annular fluorescent body 7 and its outside diameter is practically identical with the outside diameter of the fluorescent body 7 is coated with the cover film 10b having properties of transmitting the excitation light and blocking fluorescent light emanating from the fluorescent body 7 is interposed between the fluorescent body 7 and the objective optical system 1. Hence, of the fluorescent light emanating from the fluorescent body 7, fluorescent light directed toward the image side can be blocked and adverse influence on an observation image, such as flare, can be obviated. Additionally, in the first embodiment, the reflecting fluorescence cutoff filter is used and thereby fluorescent light directed toward the image side is reflected and used for illumination, which is efficient.

According to the illumination light application structure of the first embodiment, since the cylindrical transparent member 11 is provided inside the openings of the fluorescent body 7 and the fluorescence cutoff filter 10, light from the observation object is received by the top surface of the transparent member 11, and thereby the extent that the entrance surface is brought closer to the observation object and observation light is blocked by the fluorescent body 7 and the fluorescence cutoff filter 10 can be reduced. Moreover, since light rays travel parallel to the optical axis inside the cylindrical transparent member 11, the observation can be carried out at a wider field angle. The periphery of the cylindrical transparent member 11 is covered with the light-blocking member 12, and therefore, of the fluorescent light emanating from the fluorescent body 7, fluorescent light directed toward the optical axis side can be blocked, with the result that observation accuracy is improved.

Also, although the illumination light application structure shown in FIG. 3A is designed so that the cylindrical transparent member 11 is provided, it may be designed so that the cylindrical transparent member 11 is not provided when a wide-field-angle observation is unnecessary. In this case, for example, as shown in FIG. 4, when the inside diameter of the fluorescence cutoff filter 10 is smaller than that of the fluorescent body 7, the light-blocking member 12 is designed to lie in the proximity of the opening of the fluorescent body 7 and the opening of the fluorescence cutoff filter 10. By doing so, of the fluorescent light emanating from the fluorescent body 7, fluorescent light directed toward the optical axis side can be blocked. When the inside diameters of the fluorescent body 7 and the fluorescence cutoff filter 10 are the same in size, the light-blocking member 12 is designed to lie inside the opening of the fluorescent body 7 and the fluorescence cutoff filter 10. In this way, the same effect as in the arrangement of FIG. 4 is secured.

The illumination light application structure shown in FIG. 3A is designed so that the fluorescence cutoff filter 10 is placed, but when the fluorescent light directed toward the image side is merely cut off by the reflecting surface of the reflecting mirror 9 and trouble due to unwanted light is not caused, it may be designed so that the fluorescence cutoff filter 10 is not placed. The objective optical system 1 may be constructed with two convex lenses, such as those shown in FIG. 4, not to speak of the SELFOC type, and may be other lenses. The image transmitting optical system 2, instead of using the relay lens, may be constructed to use a fiber, such as an image guide fiber or an image conduit fiber shown, for example, in FIG. 10.

Second Embodiment

Figure 11:
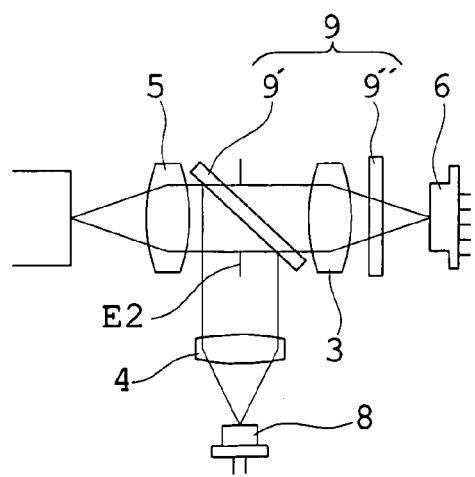
FIG. 11 is an explanatory view of essential parts of the endoscope provided with the illumination light application structure according to a second embodiment in the present invention, showing schematically the optical arrangement of the irradiation means.

FIG. 11 is an explanatory view of essential parts of the endoscope provided with the illumination light application structure according to the second embodiment in the present invention, showing schematically the optical arrangement of the irradiation means. In the illumination light application structure in the endoscope of the second embodiment, the irradiation means 9 is constructed with a half mirror 9' obliquely placed in the proximity of the position of the pupil E2 conjugate with the entrance pupil E1 of the objective optical system 1 so that the excitation light emitted form the light source 8 is reflected toward the objective-optical-system-1 side, and a barrier filter 9'' having the property of blocking light emitted from the light source 8 is placed on the image side of the half mirror 9'. Other features are almost the same as in the illumination light application structure of the first embodiment.

In the illumination light application structure of the second embodiment constructed as mentioned above, the light emitted from the light source 8 is incident on the half mirror 9' through the illumination optical system 4. Light reflected by the half mirror 9' is incident on the objective optical system (omitted from FIG. 11) through the imaging optical system 5 and the image transmitting optical system (omitted form FIG. 11). The light incident on the objective optical system enters the fluorescent body (omitted from FIG. 11) through the fluorescence cutoff filter (omitted from FIG. 11) at the position of the entrance pupil (omitted from FIG. 11) of the objective optical system. Whereby, the fluorescent body is excited to emit fluorescent light. Of the fluorescent light emanating from the fluorescent body, fluorescent light directed toward the object side is used as illumination light for illumination of the observation object.

Also, fluorescent light directed toward the image side is blocked by the fluorescence cutoff filter. Fluorescent light directed toward the optical axis side is blocked by the light-blocking member (omitted from FIG. 11) with which the periphery of the cylindrical transparent member (omitted from FIG. 11) is covered. In the illumination light application structure shown in FIG. 11, however, the excitation light reflected by the half mirror 9' passes through the cylindrical transparent member and irradiates the observation object. Light from the observation object is incident on the cylindrical transparent member and enters the half mirror 9' through the objective optical system, the image transmitting optical system, and the imaging optical system 5. The light transmitted through the half mirror 9' is imaged on the image pickup surface of the image sensor 6 through the imaging optical system 3 and the barrier filter 9''. At this time, the barrier filter 9'' blocks excitation light emitted from the light source 8 and reflected by the observation object, of the light from the observation object, and transmits light of other wavelengths. According to the illumination light application structure of the second embodiment, therefore, almost the same effect in the illumination light application structure of the first embodiment is obtained by using the existing filter.

Further, as a modified example of the illumination light application structure of the second embodiment, the irradiation means 9 may be constructed with a wavelength selective member (for example, a band-pass filter or an etalon) having properties of reflecting the light emitted from the light source 8 and transmitting light of remaining wavelengths and obliquely placed in the proximity of the position of the pupil E2 conjugate with the entrance pupil of the objective optical system so as to reflect the light from the light source 8 toward the objective optical system side. When the irradiation means 9 is constructed as mentioned above, space for placing the barrier filter 9'' can be eliminated and the number of parts constituting the irradiation means 9 can be reduced.

Also, it is only necessary that at least a part of excitation light is incident on the fluorescent body, and in this case, the irradiation means 9 may not necessarily be placed in the proximity of the pupil E2. The irradiation means may also be constructed so that the light emitted from the light source 8 is transmitted through the half mirror 9' and the light from the observation object is reflected by the half mirror 9'.

Third Embodiment

Figure 12A:
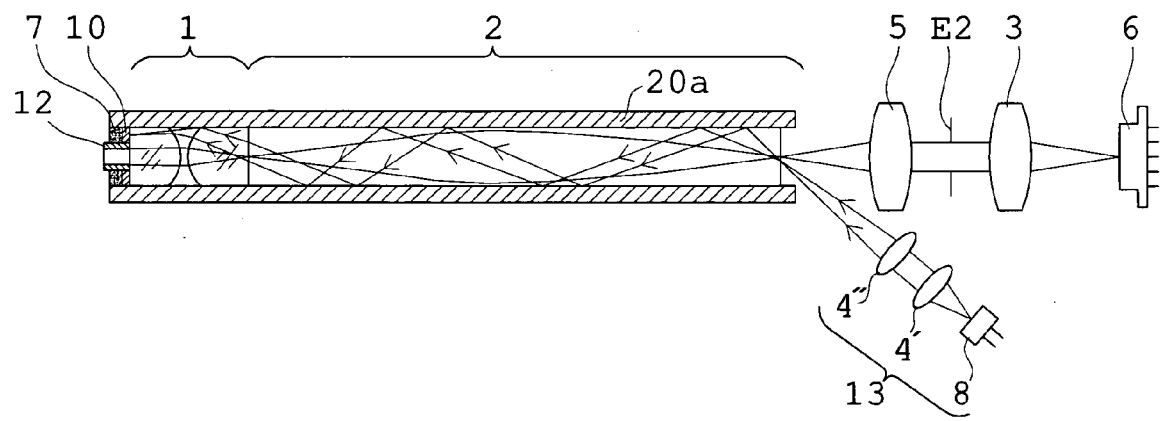
FIGS. 12A and 12B are explanatory views of the endoscope provided with the illumination light application structure according to a third embodiment in the present invention, showing a schematical optical arrangement of the endoscope and the arrangement of light sources relative to the image transmitting optical system, looking from the image side, respectively.
Figure 12B:
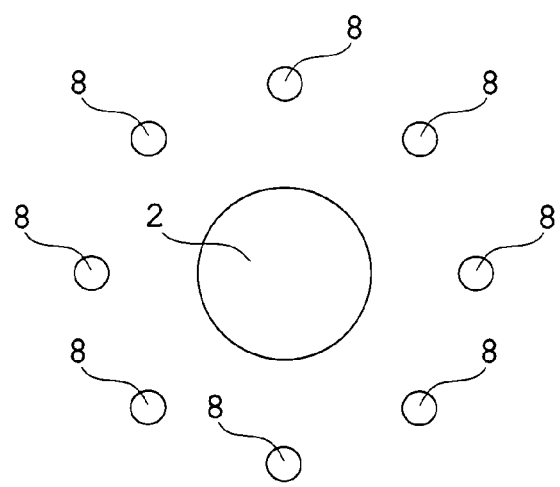
Figure 13:
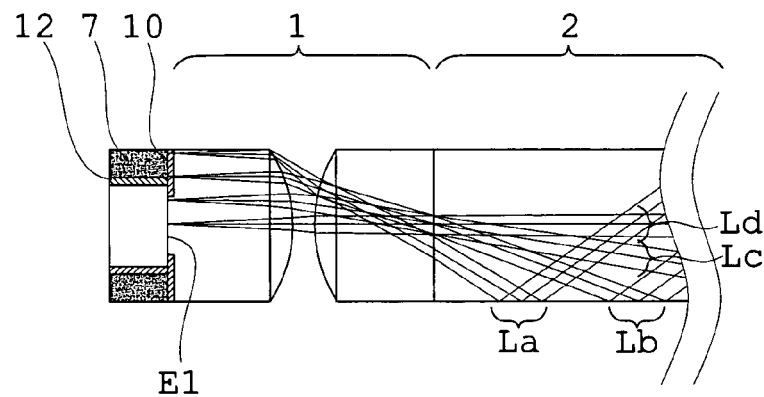
FIG. 13 is a partially enlarged explanatory view showing a trace where the fluorescent body is irradiated with excitation light at the distal end in the illumination light application structure of the endoscope of FIGS. 12A and 12B.

FIGS. 12A and 12B are explanatory views of the endoscope provided with the illumination light application structure according to the third embodiment in the present invention, showing a schematical optical arrangement of the endoscope and the arrangement of light sources relative to the image transmitting optical system, looking from the image side, respectively. FIG. 13 is a partially enlarged explanatory view showing a trace where the fluorescent body is irradiated with excitation light at the distal end in the illumination light application structure of the endoscope of FIGS. 12A and 12B.

In the illumination light application structure of the third embodiment, the image transmitting optical system 2 is such that its side is constructed with a specular SELFOC lens. The irradiation means are constructed with illumination optical systems 4' and 4'', and a plurality of illumination sections 13 including the light sources 8 and the irradiation means are annularly arranged. Each of the illumination sections 13 is placed so that an illumination optical axis obliquely intersects the optical axis of the image transmitting optical system 2, on which illumination light is incident.

In each of the illumination sections 13, the position of its placement is adjusted so that light emerging from the illumination section 13 and incident on the image transmitting optical system 2 repeatedly undergoes total reflection from the side of the image transmitting optical system 2 and is incident on the fluorescent body 7.

For example, as illustrated in FIG. 13, light beams passing through the objective optical system 1 through the image transmitting optical system 2 from the illumination sections 13 are taken as La, Lb, Lc, and Ld. Here, the light beam Ld indicates the one that the illumination optical axis does not intersect the optical axis of the image transmitting optical system 2, namely, that passes through the objective optical system 1 when the illumination optical axis is coaxially provided. When the illumination sections 13 are arranged so that the illumination optical axis obliquely intersects the optical axis of the image transmitting optical system 2, on which illumination light is incident, light beams passing through the objective optical system 1, for example, as indicated by light beams La, Lb, and Lc, travel obliquely with respect to the optical axis of the objective optical system 1 and pass through positions deviating from the optical axis of the objective optical system 1 at the position of the entrance pupil E1 of the objective optical system 1. Here, the light beams La and Lb pass through the outside of the entrance pupil E1 of the objective optical system 1 at the position of the entrance pupil E1 of the objective optical system 1.

Also, a reflecting film may be provided on the side of the image transmitting optical system 2 so that the light beams are reflected toward the optical axis side and in each of the illumination sections 13, the position of its placement is adjusted so that light emitted from the illumination sections 13 and incident on the image transmitting optical system 2 is repeatedly reflected by the reflecting surface of the side of the image transmitting optical system 2 and is incident on the fluorescent body 7. Other features are almost the same as in the illumination light application structure of the first embodiment.

In the illumination light application structure of the third embodiment constructed as mentioned above, light from an ordinary observation object, after passing through the objective optical system 1, travels without undergoing reflection from the side of the image transmitting optical system 2 and is imaged on the image pickup surface of the image sensor 6 through the imaging optical systems 5 and 3. In this case, when light, such as that causing a noise and flare, is contained in light passing through the objective optical system 1, the light is reflected by the side of the image transmitting optical system 2 to reach the imaging optical systems, but a stop is placed at the pupil E2 conjugate with the entrance pupil E1 and thereby it is possible to remove the light.

In each of the illumination sections 13, light emitted from the light source 8 is incident on the image transmitting optical system 2 through the illumination optical systems 4' and 4". The light incident on the image transmitting optical system 2 is reflected by the side of the image transmitting optical system 2 to enter the objective optical system 1 and is incident on the annular fluorescence cutoff filter 10 as an annular light beam at the position of the entrance pupil E1 of the objective optical system 1. The light incident on the fluorescence cutoff filter 10 is transmitted through the cover film 10b and enters the annular fluorescent body 7. Whereby, the fluorescent body 7 is excited to emit fluorescent light. Of the fluorescent light emitted from the fluorescent body 7, fluorescent light directed toward the object side is used as illumination light for illumination of the observation object. Also, fluorescent light directed toward the image side is blocked by the fluorescence cutoff filter 10. Fluorescent light directed toward the optical axis side of the objective optical system 1 is blocked by the light-blocking member 12. Also, it is not necessary that the illumination sections 13 are arranged over the entire perimeter as in FIG. 12B, and they may be arranged over only a part thereof. This is because, by the property that a light beam is spread in an annular shape while repeating the internal reflection of the SELFOC lens, a light beam from a part of the illumination sections is formed into an annular shape and is incident on the objective optical system. Even in the illumination light application structure of the third embodiment, therefore, almost the same effect as in the illumination light application structure of the first embodiment is brought about.

Fourth Embodiment

Figure 14A:
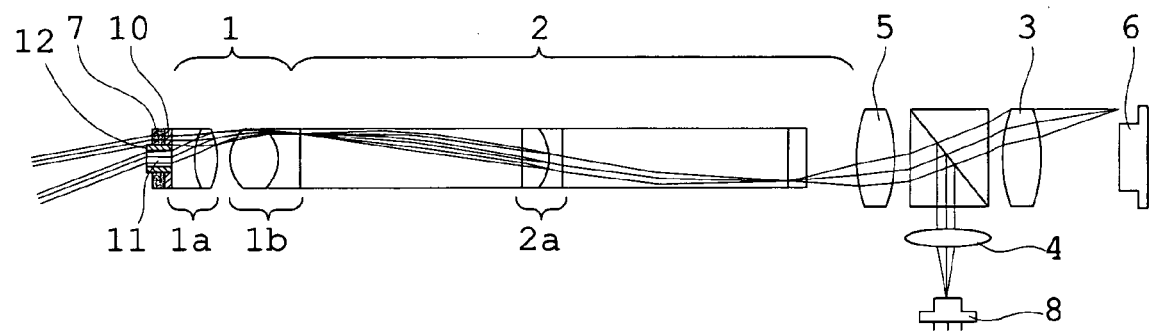
FIGS. 14A and 14B are explanatory views of the endoscope provided with the illumination light application structure according to a fourth embodiment in the present invention, showing a schematic optical arrangement of the endoscope and the arrangement of light sources in the endoscope of FIG. 14A, respectively.
Figure 14B:
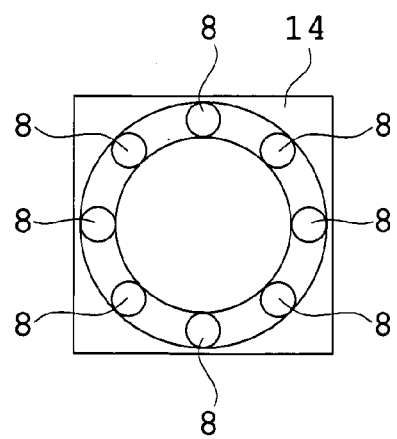

FIGS. 14A and 14B are explanatory views of the endoscope provided with the illumination light application structure according to the fourth embodiment in the present invention, showing a schematic optical arrangement of the endoscope and the arrangement of light sources in the endoscope of FIG. 14A, respectively. In the illumination light application structure of the fourth embodiment, the image transmitting optical system 2 is constructed with the SELFOC lens. The irradiation means, as shown in FIG. 14A, provides lenses constituting the objective optical system 1 and the image transmitting optical system 2 with chromatic aberration producing means such as cemented lenses 1a, 1b, and 2a, and as shown in FIG. 14B, is constructed by annularly arranging a plurality of light sources 8 so that their optical axes are located around the optical axis of the objective optical system 1.

The cemented lenses 1a, 1b, and 2a for the chromatic aberration producing means are constructed so that the annular fluorescent body is irradiated with excitation light from the light sources 8 through optical paths different from those of light of wavelengths other than the excitation light due to a color error action. Also, when the fluorescent body 7 can be irradiated with the excitation light through optical paths different from those of light of wavelengths other than the excitation light due to the color error action, the cemented lenses for the chromatic aberration producing means may be provided only in the objective optical system 1, not in the image transmitting optical system 2. Alternatively, they may be provided at arbitrary positions on the optical path between the fluorescent body 7 and the light sources 8, excluding the objective optical system 1 and the image transmitting optical system 2.

Further, in the illumination light application structure of the fourth embodiment, a wavelength selective member 14 having properties of reflecting light of wavelengths emitted from the plurality of light sources 8 annularly arranged and transmitting light of remaining wavelengths is obliquely placed in the proximity of the position of the pupil E2 conjugate with the entrance pupil E1 of the objective optical system 1. Other features are almost the same as in the illumination light application structure of FIG. 3A.

In the illumination light application structure of the fourth embodiment constructed as the foregoing, light emitted from the plurality of light sources 8 annularly arranged is reflected toward the objective-optical-system-1 side by the wavelength selective member 14 through the illumination optical system 4 and is incident as annular light beams on the objective optical system 1 through the image transmitting optical system 2. The light leaving the objective optical system 1 is incident on the annular fluorescence cutoff filter 10 and is transmitted through the cover film 10b to enter the annular fluorescent body 7. Whereby, the fluorescent body 7 is excited to emit fluorescent light. Of the fluorescent light emitted from the fluorescent body 7, fluorescent light directed toward the object side is used as illumination light for illumination of the observation object. Also, fluorescent light directed toward the image side is blocked by the fluorescence cutoff filter 10. Fluorescent light directed toward the optical axis side of the objective optical system 1 is blocked by the light-blocking member 12.

Light from the observation object is incident on the cylindrical transparent member 11 and then on the imaging optical system 5 through the objective optical system 1 and the image transmitting optical system 2. Light other than wavelengths emitted from the light sources 8 as preset wavelengths used for the observation is transmitted through the wavelength selective member 14 and is imaged on the image pickup surface of the image sensor 6 through the imaging optical system 3. At this time, due to the color error action caused by passing through the cemented lens 2a placed in the image transmitting optical system 2 and the cemented lenses 1b and 1a arranged in the objective optical system 1, the light emitted from the light sources 8 travels through optical paths different from an optical path along which light other than this light, for example, light of wavelength used for an ordinary observation passes through these cemented lenses. Consequently, the color error action of the cemented lenses is increased so that the optical paths of light emitted from the light sources 8 are considerably separated from those of light of other wavelengths and the fluorescent body 7 located on the periphery of the entrance pupil E1 is irradiated. Whereby, the optical path of the observation system can be made largely different from that of the illumination system, and a favorable observation image in which unwanted light is not mixed is obtained. Other functions and effects are nearly the same as in the illumination light application structure of the first embodiment.

Also, although in the arrangement shown in FIGS. 14A and 14B the wavelength selective member 14 is provided so that the light emitted from the light sources 8 is not incident on the imaging-optical-system-3 side, a half-mirror may be provided instead of the wavelength selective member 14. Even in the arrangement in which the half mirror is provided, when the optical path of the observation system is made largely different from that of the illumination system to such an extent that the color error action of the cemented lenses is increased and the light emitted from the light sources 8 does not enter the optical path of the observation system, a favorable observation image in which unwanted light is not mixed is obtained as in the arrangement provided with the wavelength selective member 14. In the arrangement of FIGS. 14A and 14B, the chromatic aberration producing means is constructed with the cemented lenses, but if the fluorescent body 7 can be irradiated with the excitation light through optical paths different from those of light of wavelengths other than the excitation light, for example, a diffraction grating may be used.

Fifth Embodiment

Figure 15A:
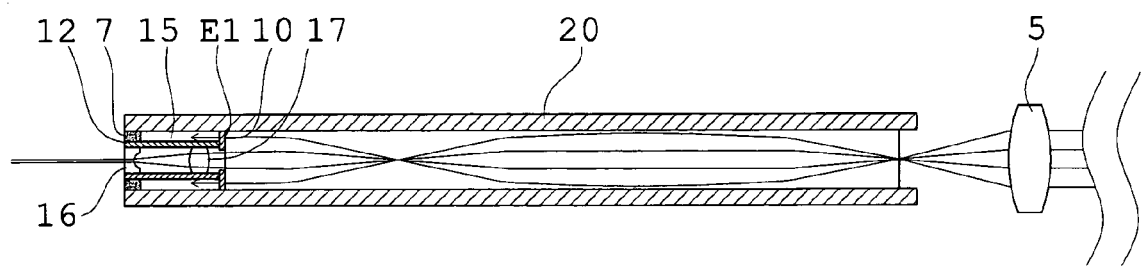
FIGS. 15A and 15B are explanatory views of the endoscope provided with the illumination light application structure according to a fifth embodiment in the present invention, showing a schematic optical arrangement of essential parts of the endoscope and a partially enlarged view of FIG. 15A, respectively.
Figure 15B:
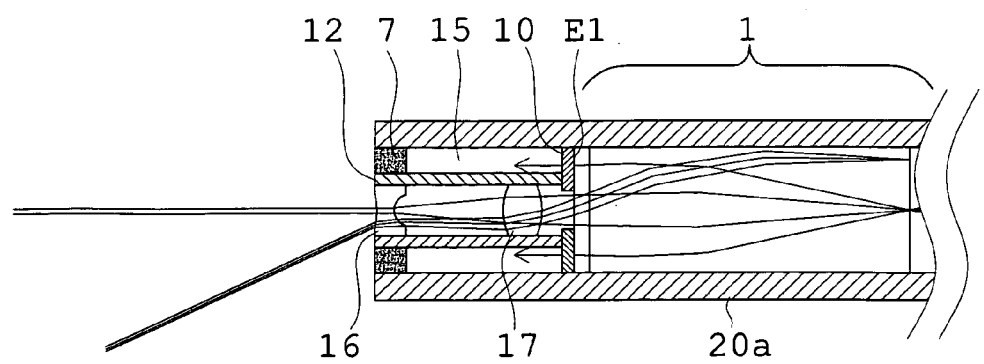

FIGS. 15A and 15B are explanatory views of the endoscope provided with the illumination light application structure according to the fifth embodiment in the present invention, showing a schematic optical arrangement of essential parts of the endoscope and a partially enlarged view of FIG. 15A, respectively. The illumination light application structure of the fifth embodiment includes the annular fluorescence cutoff filter 10 configured with an inside diameter smaller than that of the fluorescent body 7 and an outside diameter practically identical with that of the fluorescent body 7 in the proximity of the position of the entrance pupil E1 of the objective optical system 1 and having properties of transmitting excitation light and blocking fluorescent light excited by the fluorescent body 7; a trans-parent member 15 configured into an annular shape that has inside and outside diameters practically identical in size with the fluorescent body 7, provided between the fluorescent body 7 and the fluorescence cutoff filter 10; and a concave lens 16 and a convex lens 17 arranged in this order from the object side inside the transparent member 15. Other features are almost the same as in the illumination light application structure of the first embodiment. Also, the other features may be made nearly equal to those of the illumination light application structure of any one of the second to fourth embodiments.

According to the illumination light application structure of the fifth embodiment constructed as the foregoing, the annular transparent member 15 is provided and thus the optical path length of the distal end of the endoscope can be extended toward the object side. Since the lenses 16 and 17 having refracting power in order of concave and convex from the object side are arranged inside the extended distal end of the endoscope, the filed angle can be made wider. Other functions and effects are almost the same as in the illumination light application structure of the first embodiment.

Sixth Embodiment

Figure 16:
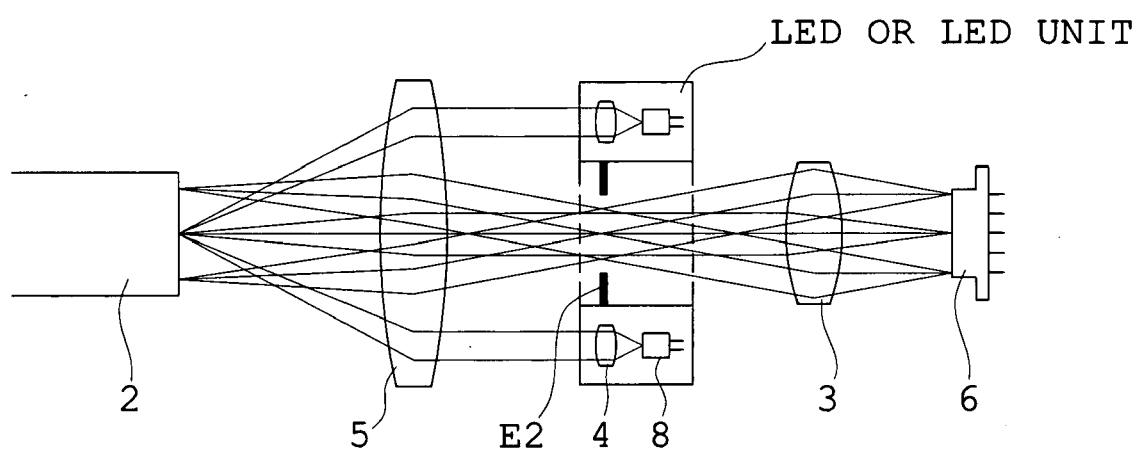
FIG. 16 is an explanatory view of essential parts of the endoscope provided with the illumination light application structure according to a sixth embodiment in the present invention, showing schematically the optical arrangement of the irradiation means.

FIG. 16 is an explanatory view of essential parts of the endoscope provided with the illumination light application structure according to the sixth embodiment in the present invention, showing schematically the optical arrangement of the irradiation means. In this embodiment, the imaging optical system 5 is made larger in diameter than that of the first embodiment and the optical axis of the illumination optical system 4 is placed parallel to that of the image transmitting optical system 2. Since the sixth embodiment is constructed in this way, there is no need to use the mirror or the half mirror as the irradiation means. Also, it is good practice to arrange a plurality of illumination optical systems 4 and a plurality of light sources 8 in an annular shape with respect to the optical axis of the objective optical system (not shown).

In any of the embodiments described above, the illumination light application structure in the endoscope using fluorescent light as illumination light has been demonstrated. However, the arrangement of the irradiation means in which the annular fluorescent body located in the proximity of the position of the entrance pupil of the objective optical system and having the inside diameter larger than the diameter of an entrance pupil of the objective optical system and the outside diameter practically identical with the diameter of a lens of the largest diameter in the objective optical system is irradiated with the light emitted from the light source through the objective optical system, shown in the illumination light application structure of each of the first and the third to six embodiments, is also applicable to the endoscope using visible light as the illumination light. Thus, in the endoscope using visible light as the illumination light, the embodiments applying the illumination light application structures of the first and the third to sixth embodiments will be described below.

Seventh Embodiment

Figure 17:
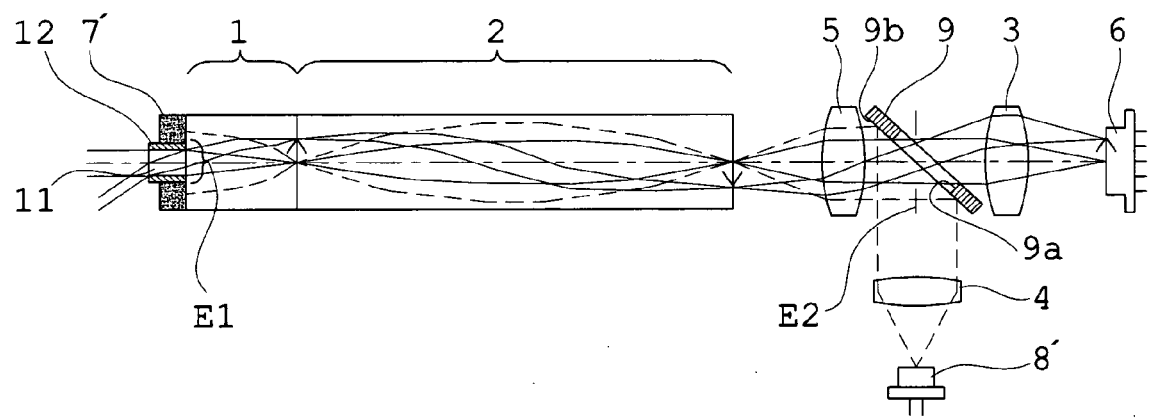
FIG. 17 is an explanatory view showing schematically the optical arrangement of the endoscope provided with the illumination light application structure according to a seventh embodiment in the present invention.
Figure 18:
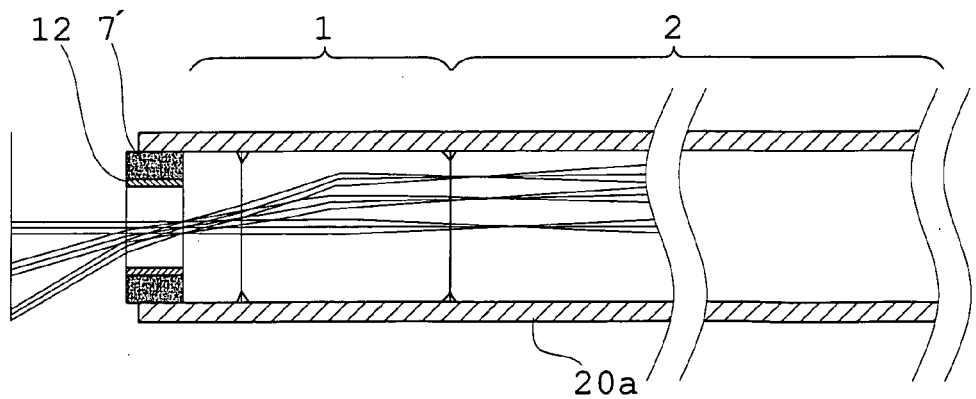
FIG. 18 is an enlarged explanatory view showing a modified example of the distal end in the illumination light application structure of the endoscope of FIG. 17.
Figure 19:
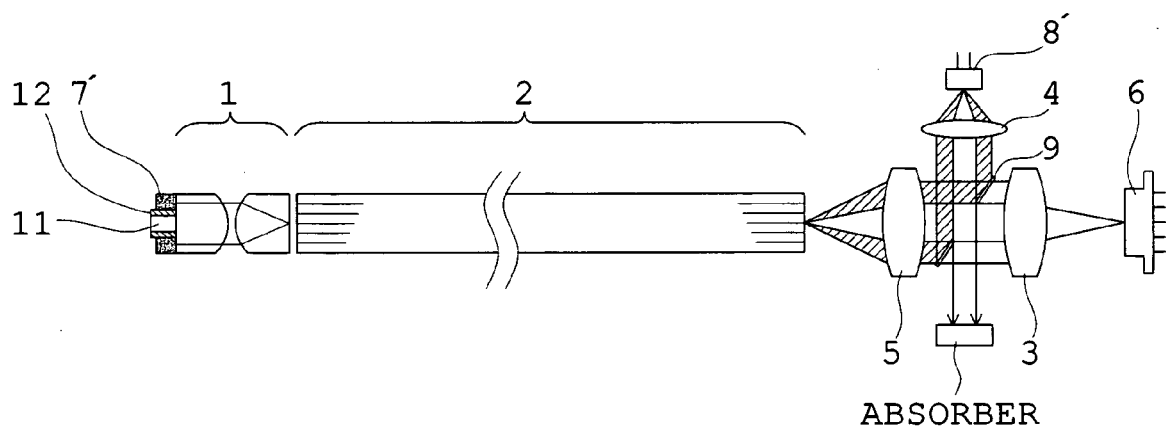
FIG. 19 is an explanatory view showing schematically an optical arrangement in the case where another image transmitting optical system is used in the illumination light application structure of the endoscope of FIG. 17.

FIG. 17 is an explanatory view showing schematically the optical arrangement of the endoscope provided with the illumination light application structure according to the seventh embodiment in the present invention. FIG. 18 is an enlarged explanatory view showing a modified example of the distal end in the illumination light application structure of the endoscope of FIG. 17. FIG. 19 is an explanatory view showing schematically an optical arrangement in the case where another image transmitting optical system is used in the illumination light application structure of the endoscope of FIG. 17. Also, like reference numerals are used for like members with respect to the endoscope of the first embodiment and their detailed explanation is omitted.

The endoscope of the seventh embodiment includes a scattering body 7', a light source 8' emitting visible light, the irradiation means 9, and the cylindrical transparent member 11. Specifically, in the endoscope of the seventh embodiment, the annular scattering body 7' is provided instead of the annular fluorescent body 7 and the annular fluorescence cutoff filter 10 in the illumination light application structure of the endoscope of the first embodiment shown in FIG. 3, and the light source 8' emitting visible light is provided instead of the light source 8 emitting excitation light. The scattering body 7' is configured into an annular shape in which its inside diameter is larger than the diameter of the entrance pupil E1 of the objective optical system 1 and its outside diameter is practically identical with the diameter of a lens having the largest diameter in the objective optical system 1. The scattering body 7 is located in the proximity of the position of the entrance pupil E1 of the objective optical system 1. The light source 8 is constructed with a visible LED and emits light of visible wavelengths. The irradiation means 9 is constructed like the irradiation means 9 in the illumination light application structure of the endoscope of the first embodiment shown in FIG. 7. The irradiation means 9 is such that an annular area (an area in which the scattering body 7' is placed) located in the proximity of the position of the entrance pupil E1 of the objective optical system 1 and having the inside diameter larger than the diameter of the entrance pupil E1 of the objective optical system 1 and the outside diameter practically identical with the diameter of a lens of the largest diameter in the objective optical system 1 is irradiated with the light emitted from the light source 8' through the objective optical system 1. Other features are nearly the same as in the endoscope of the first embodiment.

In the endoscope provided with the illumination light application structure of the seventh embodiment constructed as the foregoing, light of visible wavelengths emitted from the light source 8' is incident on the reflecting mirror 9 for the irradiation means through the illumination optical system 4. Of a light beam incident on the reflecting mirror 9, light incident on the opening 9a passes through the opening 9a as it is. This transmitted light can be absorbed by placing the light-absorbing member omitted from the figure. On the other hand, light incident on the reflecting surface 9b is reflected toward the objective-optical-system-1 side and enters the objective optical system 1 as an annular light beam through the imaging optical system 5 and the image transmitting optical system 2. The light entering the objective optical system 1 passes through the outside position of the entrance pupil E1 at the position of the entrance pupil E1 of the objective optical system 1 and is incident on the scattering body 7'. The scattering body 7' scatters the incident light and makes this light to emerge therefrom. Of the scattered light emanating from the scattering body 7', light directed toward the object side is used as illumination light for illumination of the observation object. Light from the illuminated observation object is incident on the cylindrical transparent member 11 and is imaged on the image pickup surface of the image sensor 6 through the objective optical system 1, the image transmitting optical system 2, and the imaging optical systems 5 and 3.

In the illumination light application structure of the seventh embodiment, as discussed above, the annular scattering body 7' configured into a size that its inside diameter is larger than the diameter of the entrance pupil E1 of the objective optical system 1 and its outside diameter is practically identical with the largest diameter of the objective optical system 1 is provided in the proximity of the position of the entrance pupil E1 of the objective optical system 1, and scattered visible light emanating from the scattering body 7' in such a way that the scattering body 7' is irradiated with light of visible wavelength through the irradiation means 9 is used as the illumination light. Specifically, even in the illumination light application structure of the seven embodiment, like the illumination light application structure of the first embodiment, the observation system and the illumination system are made coaxial in respect of the objective optical system and the image transmitting optical system and an outside region unnecessary for the observation at the top of the observation system provided with the objective optical system is used as the optical path of the illumination system.

According to the illumination light application structure of the seventh embodiment, therefore, like the illumination light application structure of the first embodiment, there is no need to provide the optical path for the illumination system around the objective optical system 1, and the optical apparatus, such as the endoscope, in which the distal end is made to have a tiny diameter to the extent impossible for the prior art described in Kokai Nos. Hei 10-216085 and Hei 4-244130, can be realized. Moreover, since it is not necessary that an illumination system optical member, such as a light guide, is eccentrically placed around the objective optical system, the occurrence of halation in the observation system caused by the problem that only one direction is brightly illuminated can be prevented. In addition, the observation system is placed at the center inside the insertion section of the distal end, and thus the occurrence of asymmetrical distortion of the observation image can also be prevented.

In the illumination light application structure of the seventh embodiment, the irradiation means 9 is constructed with the annular reflecting mirror which includes the opening 9a having the diameter practically identical with the diameter of the pupil E2 conjugate with the entrance pupil E1 of the objective optical system 1 in a state where the reflecting mirror is obliquely placed and the reflecting surface 9b reflecting the light emitted from the light source 8' toward the objective-optical-system-1 side, provided on the periphery of the opening 9a, and which is obliquely placed in the proximity of the position of the pupil E2 conjugate with the entrance pupil E1 of the objective optical system 1. Hence, the light emitted form the light source 8' can be made incident on the scattering body 7 in such a way that the light does not enter the entrance pupil E1 of the objective optical system 1 as far as possible. The observation light beam from the observation object is such that light passing through the entrance pupil E1 of the objective optical system 1 goes through the opening 9a and is imaged on the image pickup surface of the image sensor 6 through the imaging optical system 3. Even though other unwanted light is produced, the light is reflected by the reflecting surface 9b and thereby the incidence of the light on the imaging optical system 3 can be prevented. Consequently, even when the optical path of the illumination system is provided in the objective optical system 1, the observation object can be illuminated without obstructing the observation in the observation system.

According to the illumination light application structure of the seventh embodiment, since the cylindrical transparent member 11 is provided in the opening of the scattering body 7', light from the observation object is received by the top surface of the transparent member 11, and thereby the extent that the entrance surface is brought closer to the observation object and observation light is blocked by the scattering body 7' can be reduced. Moreover, since light rays travel parallel to the optical axis inside the cylindrical transparent member 11, the observation can be carried out at a wider field angle. The periphery of the cylindrical transparent member 11 is covered with the light-blocking member 12, and therefore, of the light emanating from the scattering body 7', fluorescent light directed toward the optical axis side can be blocked, with the result that observation accuracy is improved. Also, although the illumination light application structure shown in FIG. 17 is designed so that the cylindrical transparent member 11 is provided, it may be designed so that the cylindrical transparent member 11 is not provided when a wide-field-angle observation is unnecessary.

The objective optical system 1 may be constructed with two convex lenses, such as those shown in FIG. 18, not to speak of the SELFOC type, and may be other lenses. The image transmitting optical system 2, instead of using the relay lens, may be constructed to use a fiber, such as an image guide fiber or an image conduit fiber shown, for example, in FIG. 19.

The illumination light application structure of the seventh embodiment, as discussed above, is designed on the premise that the visible light is used as the illumination light in the endoscope, and is different in this respect from the illumination light application structure of the first embodiment which is designed on the premise that the fluorescent light is used as the illumination light in the endoscope. However, the irradiation means is constructed so that the annular area having the inside diameter larger than the diameter of the entrance pupil of the objective optical system and the outside diameter practically identical with the diameter of a lens of the largest diameter in the objective optical system is irradiated with the light emitted from the light source through the objective optical system, in the proximity of the position of the entrance pupil of the objective optical system, and a fundamental idea for solving the problem in the present invention and the function and effect are almost the same as in the illumination light application structure of the first embodiment.

Also, in the illumination light application structure of the seventh embodiment based on the premise that the visible light is used as the illumination light in the endoscope, a brighter observation image is obtained than in the illumination light application structure of the first embodiment based on the premise that the fluorescent light is used as the illumination light in the endoscope. On the other hand, in the illumination light application structure of the present invention based on the premise that the fluorescent light is used as the illumination light in the endoscope like the illumination light application structure of the first embodiment, an illumination wavelength for irradiating the observation object is different from an observation wavelength for observing the observation object, and hence the occurrence of halation in the observation system can be considerably prevented, as compared with the illumination light application structure of the seventh embodiment in which the same visible wavelength is used for the illumination wavelength and the observation wavelength.

Eighth Embodiment

Figure 20A:
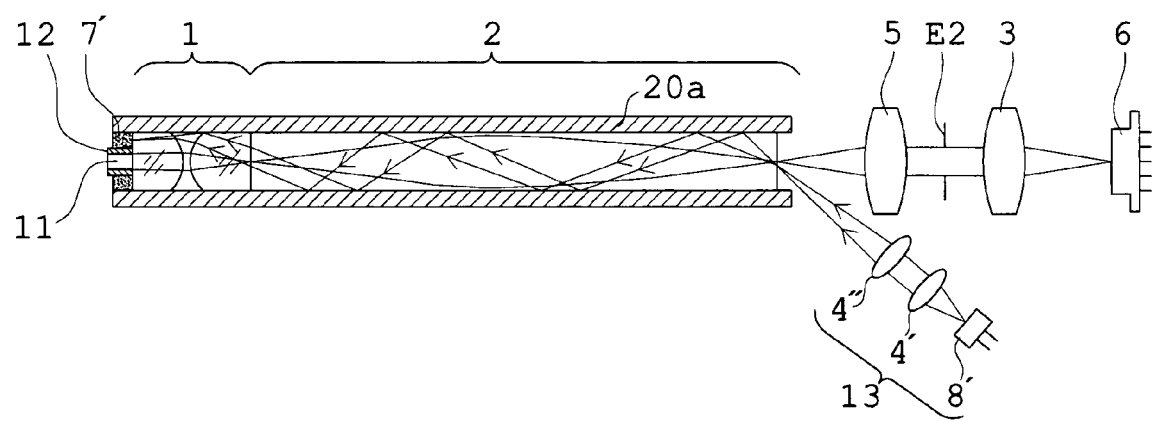
FIGS. 20A and 20B are explanatory views of the endoscope provided with the illumination light application structure according to an eighth embodiment in the present invention, showing a schematical optical arrangement of the endoscope and the arrangement of light sources relative to the image transmitting optical system, looking from the image side, respectively.
Figure 20B:
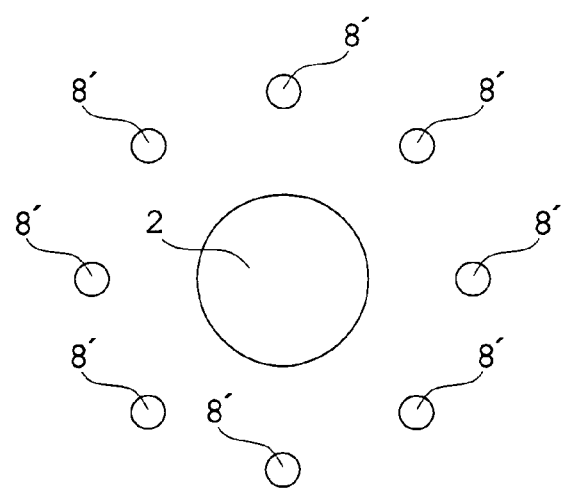
Figure 21:
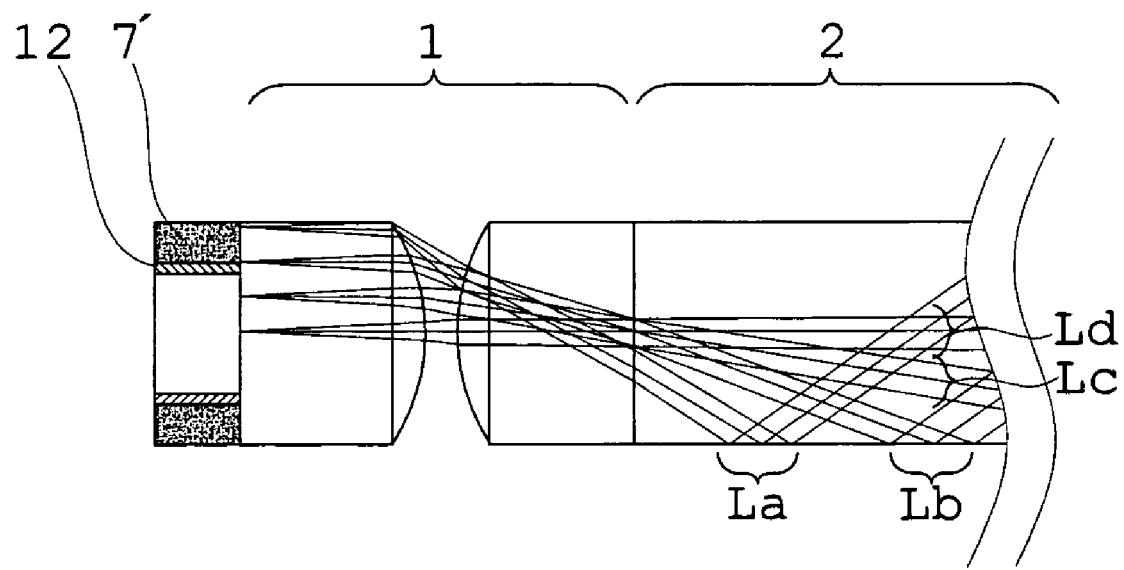
FIG. 21 is a partially enlarged explanatory view showing a trace where the scattering body is irradiated with a light beam of a visible wavelength from the light source at the distal end in the illumination light application structure of the endoscope of FIG. 20A.

FIGS. 20A and 20B are explanatory views of the endoscope provided with the illumination light application structure according to the eighth embodiment in the present invention, showing a schematical optical arrangement of the endoscope and the arrangement of light sources relative to the image transmitting optical system, looking from the image side, respectively. FIG. 21 is a partially enlarged explanatory view showing a trace where the scattering body is irradiated with a light beam of a visible wavelength from the light source at the distal end in the illumination light application structure of the endoscope of FIG. 20A.

The endoscope of the eighth embodiment includes the annular scattering body 7', instead of the annular fluorescent body 7 and the annular fluorescence cutoff filter 10 in the illumination light application structure of the endoscope of the third embodiment shown in FIGS. 14A and 14B, and the light source 8' emitting visible light, instead of the light source 8 emitting excitation light. The scattering body 7' is configured into an annular shape in which its inside diameter is larger than the diameter of the entrance pupil E1 of the objective optical system 1 and its outside diameter is practically identical with the diameter of a lens having the largest diameter in the objective optical system 1. The scattering body 7' is located in the proximity of the position of the entrance pupil E1 of the objective optical system 1. The light source 8' is constructed with a visible LED and emits visible light.

In the illumination light application structure of the eighth embodiment, the image transmitting optical system 2 is constructed with a SELFOC lens whose side is specular. The irradiation means are constructed with illumination optical systems 4' and 4'', and a plurality of illumination sections 13 including the light sources 8 and the irradiation means are annularly arranged. Each of the illumination sections 13 is placed so that an illumination optical axis obliquely intersects the optical axis of the image transmitting optical system 2, on which illumination light is incident.

Ninth Embodiment

Figure 22A:
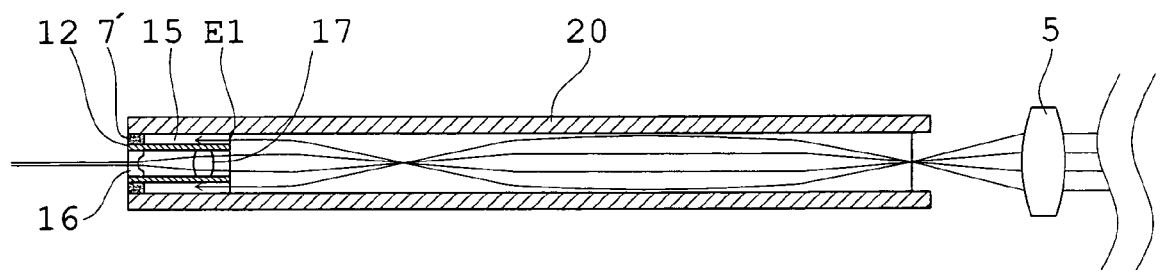
FIGS. 22A and 22B are explanatory views of the endoscope provided with the illumination light application structure according to a ninth embodiment in the present invention, showing a schematic optical arrangement of essential parts of the endoscope and a partially enlarged view of FIG. 22A, respectively.
Figure 22B:
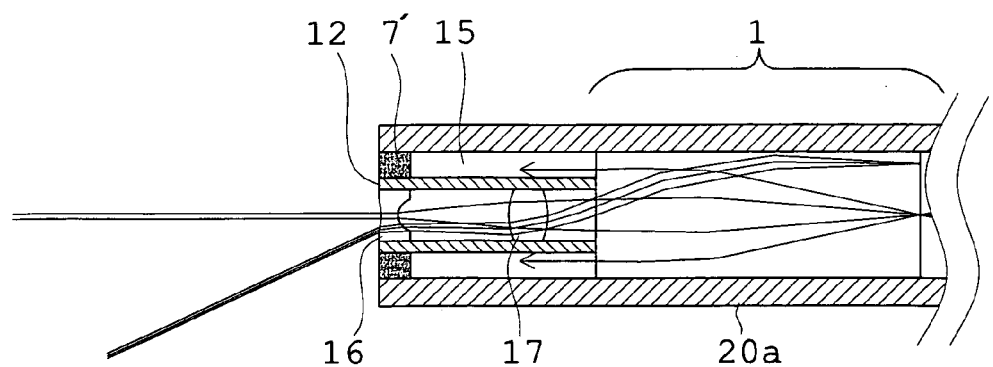

FIGS. 22A and 22B are explanatory views of the endoscope provided with the illumination light application structure according to the ninth embodiment in the present invention, showing a schematic optical arrangement of essential parts of the endoscope and a partially enlarged view of FIG. 22A, respectively.

The endoscope of the eighth embodiment includes the scattering body 7', instead of the annular fluorescent body 7 and the annular fluorescence cutoff filter 10 in the illumination light application structure of the endoscope of the fifth embodiment shown in FIGS. 15A and 15B, and the light source 8' emitting visible light, instead of the light source 8 emitting excitation light. The scattering body 7' is configured into an annular shape in which its inside diameter is larger than the diameter of the entrance pupil E1 of the objective optical system 1 and its outside diameter is practically identical with the diameter of a lens having the largest diameter in the objective optical system 1. The scattering body 7' is located in the proximity of the position of the entrance pupil E1 of the objective optical system 1. The light source 8' is constructed with a visible LED and emits visible light.

The illumination light application structure of the ninth embodiment includes the transparent member 15 configured into an annular shape of inside and outside diameters practically identical in size with the scattering body 7' in the proximity of the position of the entrance pupil E1 of the objective optical system 1 and the concave lens 16 and the convex lens 17 arranged in this order from the object side inside the transparent member 15. Other features are almost the same as in the illumination light application structure of the first embodiment. Also, the other features may be made nearly equal to those of the illumination light application structure of any one of the second to fourth embodiments.

According to the illumination light application structure of the ninth embodiment constructed as in the foregoing, the annular transparent member 15 is provided and thus the optical path length of the distal end of the endoscope can be extended toward the object side. Since the lenses 16 and 17 having refracting power in order of concave and convex from the object side are arranged inside the extended distal end of the endoscope, the filed angle can be made wider. Other functions and effects are almost the same as in the illumination light application structure of the seventh embodiment.

Tenth Embodiment

Figure 23:
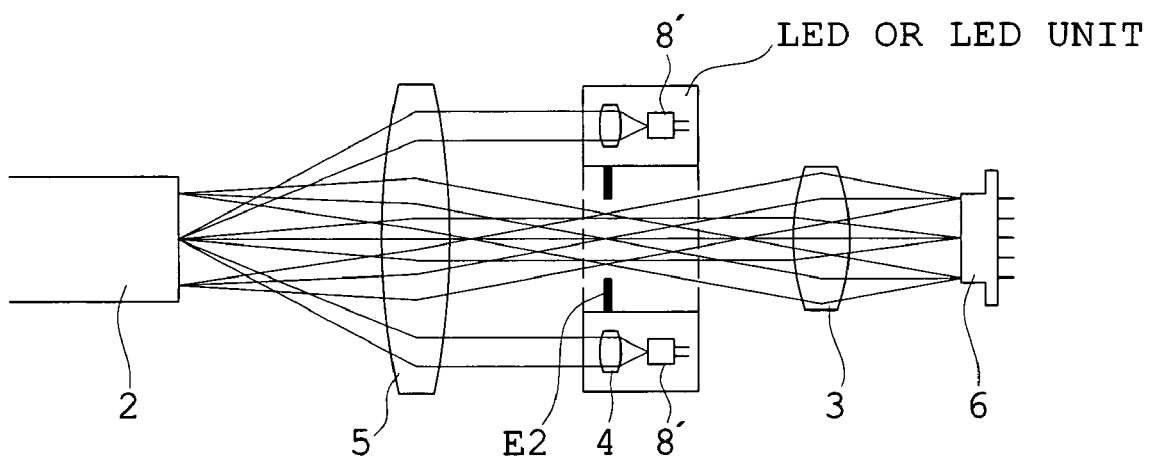
FIG. 23 is an explanatory view of essential parts of the endoscope provided with the illumination light application structure according to a tenth embodiment in the present invention, showing schematically the optical arrangement of the irradiation means.

FIG. 23 is an explanatory view of essential parts of the endoscope provided with the illumination light application structure according to the tenth embodiment in the present invention, showing schematically the optical arrangement of the irradiation means. In the illumination light application structure of the tenth embodiment, the imaging optical system 5 is made larger in diameter than that of the seventh embodiment and the optical axis of the illumination optical system 4 is placed parallel to that of the image transmitting optical system 2. A plurality of illumination optical systems 4 and a plurality of light sources 8' are annularly arranged with respect to the optical axis of the objective optical system (not shown). Other features are nearly the same as in the illumination light application structure of the seventh embodiment. Since the tenth embodiment is constructed as mentioned above, there is no need to used the mirror or the half mirror as the irradiation means.

Eleventh Embodiment

Figure 24:
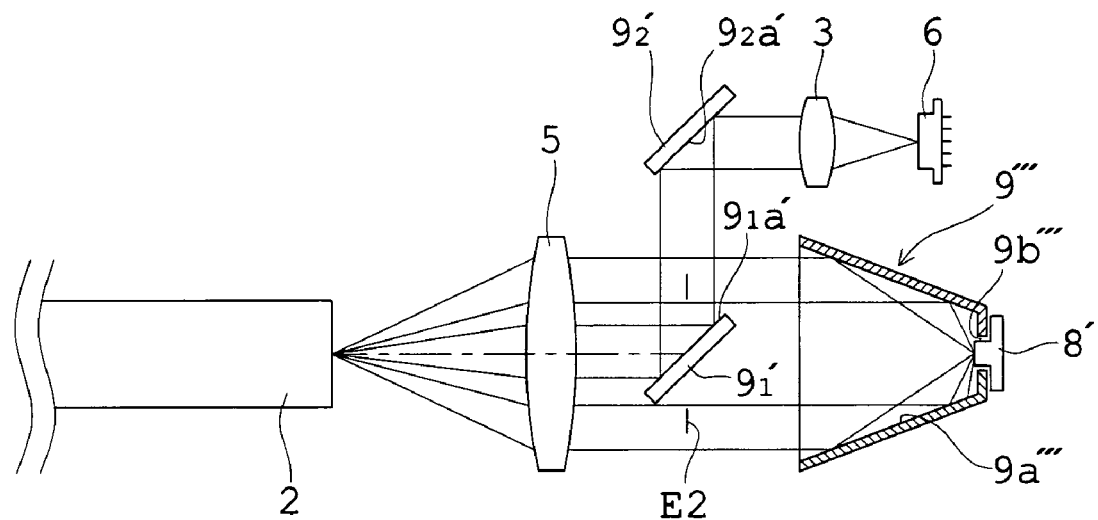
FIG. 24 is an explanatory view of essential parts of the endoscope provided with the illumination light application structure according to an eleventh embodiment in the present invention, showing schematically the optical arrangement of the irradiation means.

FIG. 24 is an explanatory view of essential parts of the endoscope provided with the illumination light application structure according to the eleventh embodiment in the present invention, showing schematically the optical arrangement of the irradiation means. The illumination light application structure of the eleventh embodiment is provided with a reflecting mirror $9_1'$ on the image side of the imaging optical system 5. The reflecting mirror $9_1'$ is obliquely placed in the proximity of the pupil E2 located at the position conjugate with the entrance pupil of the objective optical system and has a reflecting surface $9_1a'$ of a diameter practically identical in size with that of the pupil conjugate with the entrance pupil of the objective optical system in a state where the reflecting mirror is obliquely placed. In addition, a reflecting surface $9_2'$ having a reflecting surface $9_2a'$ is interposed between the reflecting mirror $9_1'$ and the imaging lens 3. The imaging lens 3 and the image sensor 6 are arranged on an optical path bent through the reflecting mirrors $9_1'$ and $9_2'$. Moreover, the illumination light application structure of the eleventh embodiment is provided with a reflecting member 9''', as the irradiation means, between the light source 8' and the reflecting mirror $9_1'$.

The reflecting member 9''' is constructed with a cylindrical member of a truncated cone shape in which its side end facing the reflecting mirror $9_1'$ is opened, its side is configured as a reflecting surface 9a''', and a light source placing hole 9b''' is provided at a side end facing the light source 8'. The reflecting surface 9a''' is constructed so that light emitted from the light source 8' is reflected in a direction parallel to the optical axis and the reflected light passes through the outside of the reflecting mirror $9_1'$. The light source placing hole 9b''' is configured into a size such that the emission part of the light source 8 can be inserted. Other features are almost the same as in the illumination light application structure of the seventh embodiment.

In the illumination light application structure of the eleventh embodiment constructed as mentioned above, light emitted from the light source 8' and incident on the reflecting surface 9a''' of the reflecting member 9''' is reflected in a direction parallel to the optical axis through the reflecting surface 9a'''. The reflected light changes to an annular parallel beam to travel through the outside of the reflecting mirror $9_1'$ and is incident on the image transmitting optical system 2 through the imaging optical system 5. Also, light emitted from the light source 8' and traveling close to the optical axis without undergoing the reflection from the reflecting surface 9a''' of the reflecting member 9''' is blocked by the reflecting mirror $9_1'$ and fails to travel toward the image transmitting optical system 2. The light incident on the image transmitting optical system 2 passes through the objective optical system (not shown) and the scattering body (not shown) and is used for the illumination of the observation object. Light from the observation object is incident on the transparent member (not shown) and is imaged on the image pickup surface of the image sensor 6 through the objective optical system (not shown), the image transmitting optical system 2, the imaging optical system 5, the reflecting mirrors $9_1'$ and $9_2'$, and the imaging optical system 3.

In the illumination light application structure of the eleventh embodiment as well, the same effect as in the illumination light application structure of the seventh embodiment is obtained. Also, the illumination light application structure of the endoscope using visible light as the illumination light may be designed to provide the light source 8 emitting the excitation light, instead of providing the light source 8' emitting the visible light in the illumination light application structure of the eleventh embodiment, and the annular fluorescent body and the annular fluorescence cutoff filter, instead of providing the transparent member, not shown. In this case, the same effect as in the illumination light application structure of the first embodiment is brought about.

Twelfth Embodiment

Figure 25:
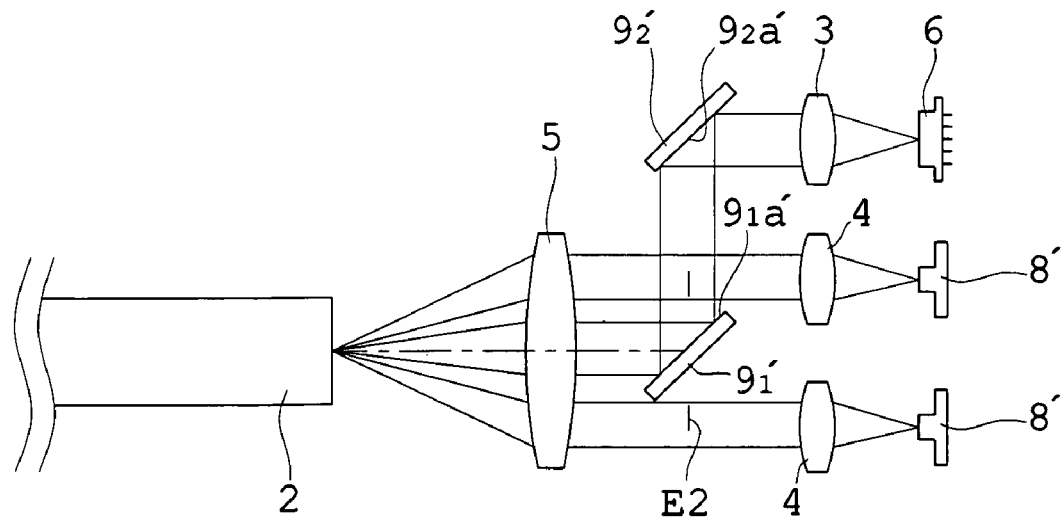
FIG. 25 is an explanatory view of essential parts of the endoscope provided with the illumination light application structure according to a twelfth embodiment in the present invention, showing schematically the optical arrangement of the irradiation means.

FIG. 25 is an explanatory view of essential parts of the endoscope provided with the illumination light application structure according to the twelfth embodiment in the present invention, showing schematically the optical arrangement of the irradiation means. The illumination light application structure of the twelfth embodiment, which is a modified example of the illumination light application structure of the eleventh embodiment, is constructed so that, instead of the reflecting member 9''' in the eleventh embodiment, a plurality of light sources 8' and a plurality of illumination optical systems 4 are annularly arranged with respect to the optical axis of the objective optical system (not shown), and individual light emitted from the light sources 8' travels through the periphery of the pupil conjugate with the entrance pupil of the objective optical system. Individual optical axes of the light sources 8' and the illumination optical systems 4 are arranged parallel to the optical axis of the objective optical system (not shown). Other features are almost the same as in the illumination light application structure of the eleventh embodiment.

According to the illumination light application structure of the twelfth embodiment constructed as mentioned above, the same effect as in the illumination light application structure of the eleventh embodiment. Also, the illumination light application structure of the endoscope using visible light as the illumination light may be designed to provide the light sources 8 emitting the excitation light, instead of providing the light sources 8' emitting the visible light in the illumination light application structure of the twelfth embodiment, and the annular fluorescent body and the annular fluorescence cutoff filter, instead of providing the transparent member, not shown. In this case, the same effect as in the illumination light application structure of the first embodiment is brought about.

Thirteenth Embodiment

Figure 26:
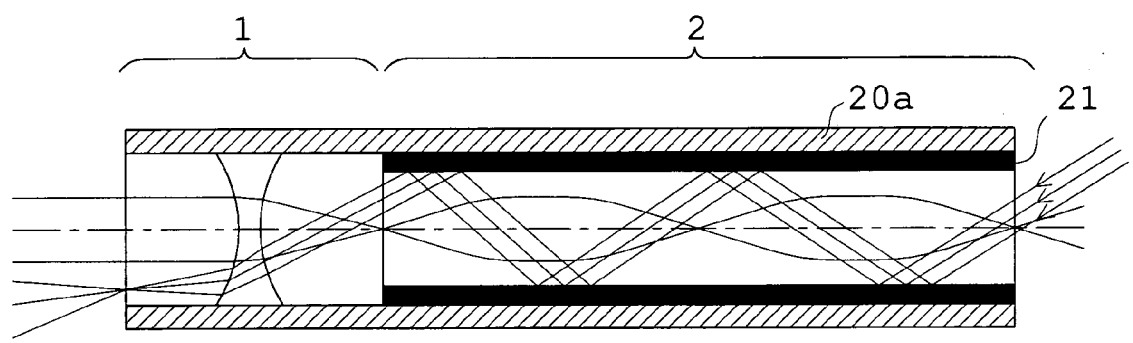
FIG. 26 is an explanatory view of essential parts of the endoscope provided with the illumination light application structure according to a thirteenth embodiment in the present invention, showing schematically the optical arrangement of the objective optical system and the image transmitting optical system.

FIG. 26 is an explanatory view of essential parts of the endoscope provided with the illumination light application structure according to the thirteenth embodiment in the present invention, showing schematically the optical arrangement of the objective optical system and the image transmitting optical system. The illumination light application structure of the thirteenth embodiment, which is a modified example of the illumination light application structure of the eighth embodiment, is provided with a low-refractive-index cladding layer 21 on the periphery of the SELFOC lens constituting the image transmitting optical system 2. The illumination light application structure of the thirteen embodiment is constructed so that the most object-side surface of the objective optical system 1 is not provided with the annular scattering body 7', the cylindrical transparent member 11, and the light-blocking member 12. Specifically, in the illumination light application structure of the thirteen embodiment, light from the light source, not shown, emitting visible light emerges from an outside annular area on the most object-side surface of the objective optical system 1 through the image transmitting optical system 2 and is used for illumination. Other features are almost the same as in the illumination light application structure of the eighth embodiment.

According to the illumination light application structure of the thirteen embodiment constructed as mentioned above, the low-refractive-index cladding layer 21 is provided on the periphery of the SELFOC lens constituting the image transmitting optical system 2, and hence it becomes easy that light incident on the SELFOC lens undergoes total reflection from the low-refractive-index cladding layer 21 and bright light with less flare is supplied. In addition, by providing the cladding layer 21 on the periphery of the SELFOC lens, the strength of the SELFOC lens is increased and becomes hard to break. Other effects are almost the same as in the illumination light application structure of the eighth embodiment.

Also, the illumination light application structure of the endoscope using visible light as the illumination light may be designed to provide the light sources 8 emitting the excitation light, instead of providing the light sources 8' emitting the visible light in the illumination light application structure of the thirteenth embodiment, and the annular fluorescent body and the annular fluorescence cutoff filter, instead of providing the transparent member, not shown. In this case, the same effect as in the illumination light application structure of the third embodiment is brought about.

As for the rest, in each of the embodiments discussed above, the illumination light application structure has been used in the endoscope provided with the image transmitting optical system, but in the endoscope failing to provide the image transmitting optical system, for example, in a video endoscope housing the objective optical system and the image sensor, such as a CCD, at the distal end, the illumination light application structure of the present invention is also applicable.

Also, although in each of the embodiments discussed above the endoscope has been provided with the illumination light application structure, the illumination light application structure of the present invention is not limited to the application to the endoscope and is applicable to any optical apparatus in which the top of the observation system is configured into a tiny diameter and the exit end of the illumination system is placed close to the top of the observation system.

What is claimed is:

1. An illumination light application structure for irradiating an observation object with illumination light in an observation optical apparatus provided with an objective optical system inside a lens barrel whose top is configured into a slender shape, the illumination light application structure comprising:
a wavelength converting element located proximate to a position of an entrance pupil of the objective optical system;
a light source emitting light whose wavelength is converted by the wavelength converting element; and
irradiation means irradiating, through the objective optical system, the wavelength converting element with the light emitted from the light source.

2. An illumination light application structure according to claim 1, wherein an image transmitting optical system including one of a relay lens, an image fiber, and a SELFOC lens is provided on an image side of the objective optical system.

3. An illumination light application structure according to claim 2, wherein the image transmitting optical system is constructed with a SELFOC lens and the SELFOC lens is provided with a low-refractive-index cladding layer on a periphery thereof.

4. An illumination light application structure according to claim 1, wherein the observation optical apparatus is an endoscope.

5. An illumination light application structure according to claim 1, wherein the light source includes an LD or LED.

6. An endoscope provided with the illumination light application structure according to claim 1.

7. An illumination light application structure for irradiating an observation object with illumination light in an observation optical apparatus provided with an objective optical system inside a lens barrel whose top is configured into a slender shape, the illumination light application structure comprising:
a fluorescent body located proximate to a position of an entrance pupil of the objective optical system;
a light source emitting light for exciting the fluorescent body; and
irradiation means irradiating the fluorescent body with the light emitted from the light source through the objective optical system.

8. An illumination light application structure according to claim 7, wherein the irradiation means is constructed with a reflecting mirror obliquely placed proximate to a position of a pupil conjugate with the entrance pupil of the objective optical system, including an opening having a diameter practically identical with a diameter of the pupil conjugate with the entrance pupil of the objective optical system in a state where the reflecting mirror is obliquely placed and a reflecting surface reflecting the light emitted from the light source toward an objective optical system side, on the periphery of the opening.

9. An illumination light application structure according to claim 7, wherein the irradiation means includes a half mirror obliquely placed proximate to a position of a pupil conjugate with the entrance pupil of the objective optical system so as to reflect the light emitted from the light source toward an objective optical system side and a barrier filter having a property of blocking the light emitted from the light source, placed on an image side of the half mirror.

10. An illumination light application structure according to claim 7, wherein the irradiation means is constructed with a wavelength selective member having properties of reflecting the light emitted from the light source and transmitting light of remaining wavelengths, obliquely placed proximate to a position of a pupil conjugate with the entrance pupil of the objective optical system so as to reflect the light from the light source toward an objective optical system side.

11. An illumination light application structure according to claim 7, wherein a fluorescence cutoff filter having properties of transmitting excitation light and blocking fluorescent light emanating from the fluorescent body is placed on an image side of the fluorescent body.

12. An illumination light application structure according to claim 11, wherein a light-blocking member is provided inside openings of the fluorescent body and the fluorescence cutoff filter.

13. An illumination light application structure according to claim 11, wherein a light-blocking member is provided inside an opening of the fluorescent body and proximate to an opening of the fluorescence cutoff filter.

14. An illumination light application structure according to claim 11, wherein a cylindrical transparent member is provided inside openings of the fluorescent body and the fluorescence cutoff filter.

15. An illumination light application structure according to claim 7, wherein a light-blocking member is provided inside an opening of the fluorescent body.

16. An illumination light application structure according to claim 7, wherein a cylindrical transparent member is provided inside an opening of the fluorescent body.

17. An illumination light application structure according to claim 7, wherein an image transmitting optical system including one of a relay lens, an image fiber, and a SELFOC lens is provided on an image side of the objective optical system.

18. An illumination light application structure according to claim 17, wherein the image transmitting optical system is constructed with the SELFOC lens and the irradiation means includes an illumination optical system having an optical axis inclined with respect to an optical axis of the SELFOC lens so that excitation light emitted from the light source is obliquely incident on an entrance surface of the SELFOC lens.

19. An illumination light application structure according to claim 18, wherein the chromatic aberration producing means includes a cemented lens or a diffraction grating.

20. An illumination light application structure according to claim 17, wherein the irradiation means includes chromatic aberration producing means placed on an optical path between the fluorescent body and the light source so that the fluorescent body is irradiated with excitation light through an optical path different from optical paths of light of wavelengths other than the excitation light due to a color error action and the light source placed to lie around the objective optical system.

21. An illumination light application structure according to claim 20, wherein the chromatic aberration producing means includes a cemented lens or a diffraction grating.

22. An illumination light application structure according to claim 17, further comprising a fluorescence cutoff filter configured into a size that is smaller in inside diameter than the fluorescent body and is practically identical in outside diameter with the fluorescent body proximate to a position of the entrance pupil of the objective optical system and having properties of transmitting excitation light and blocking fluorescent light emanating from the fluorescent body; a transparent member configured into an annular shape that has inside and outside diameters practically identical in size with the fluorescent body, provided between the fluorescent body and the fluorescence cutoff filter; and a concave lens and a convex lens arranged in this order from an object side inside the transparent member.

23. An illumination light application structure according to claim 7, wherein the irradiation means includes chromatic aberration producing means placed on an optical path between the fluorescent body and the light source so that the fluorescent body is irradiated with excitation light through an optical path different from optical paths of light of wavelengths other than the excitation light due to a color error action and the light source placed to lie around the objective optical system.

24. An illumination light application structure according to claim 7, further comprising a fluorescence cutoff filter configured into a size that is smaller in inside diameter than the fluorescent body and is practically identical in outside diameter with the fluorescent body proximate to a position of the entrance pupil of the objective optical system and having properties of transmitting excitation light and blocking fluorescent light emanating from the fluorescent body; a transparent member configured into an annular shape that has inside and outside diameters practically identical in size with the fluorescent body, provided between the fluorescent body and the fluorescence cutoff filter; and a concave lens and a convex lens arranged in this order from an object side inside the transparent member.

25. An illumination light application structure according to claim 7, wherein the observation optical apparatus is an endoscope.

26. An illumination light application structure according to claim 7, wherein the light source includes an LD or LED.

27. An endoscope provided with the illumination light application structure according to claim 7.

28. An illumination light application structure for irradiating an observation object with illumination light in an observation optical apparatus provided with an objective optical system inside a lens barrel whose top is configured into a slender shape, the illumination light application structure comprising:
   an annular fluorescent body located proximate to a position of an entrance pupil of the objective optical system, having a size that an inside diameter is larger than a diameter of the entrance pupil of the observation optical system and an outside diameter is practically identical with a diameter of a lens of a largest diameter in the objective optical system;
   a light source emitting light for exciting the fluorescent body; and
   irradiation means irradiating the fluorescent body with the light emitted from the light source through the objective optical system.

29. An illumination light application structure according to claim 28, wherein the irradiation means is constructed with a reflecting mirror obliquely placed proximate to a position of a pupil conjugate with the entrance pupil of the objective optical system, including an opening having a diameter practically identical with a diameter of the pupil conjugate with the entrance pupil of the objective optical system in a state where the reflecting mirror is obliquely placed and a reflecting surface reflecting the light emitted from the light source toward an objective optical system side, provided on a periphery of the opening.

30. An illumination light application structure according to claim 28, wherein the irradiation means is provided with a reflecting mirror obliquely placed proximate to a position of a pupil conjugate with the entrance pupil of the objective optical system, including a reflecting surface having a diameter practically identical with a diameter of the pupil conjugate with the entrance pupil of the objective optical system in a state where the reflecting mirror is obliquely placed and is constructed so that the fluorescent body is irradiated through the objective optical system with light passing through a periphery of the reflecting mirror, of the light emitted from the light source.

31. An illumination light application structure according to claim 28, wherein the light source includes a plurality of light source elements annularly arranged with respect to an optical axis of the objective optical system and the irradiation means is configured so that light beams emitted from the plurality of light source elements pass through an annular region outside a pupil that is conjugate with the entrance pupil of the objective optical system.

32. An illumination light application structure according to claim 28, wherein the irradiation means is constructed with a wavelength selective member having properties of reflecting the light emitted from the light source and transmitting light of remaining wavelengths, obliquely placed proximate to a position of a pupil conjugate with the entrance pupil of the objective optical system so as to reflect the light from the light source toward an objective optical system side.

33. An illumination light application structure according to claim 28, wherein a fluorescence cutoff filter having properties of transmitting excitation light and blocking fluorescent light emanating from the fluorescent body is placed on an image side of the fluorescent body.

34. An illumination light application structure according to claim 33, wherein a light-blocking member is provided inside openings of the fluorescent body and the fluorescence cutoff filter.

35. An illumination light application structure according to claim 33, wherein a light-blocking member is provided inside an opening of the fluorescent body and proximate to an opening of the fluorescence cutoff filter.

36. An illumination light application structure according to claim 33, wherein a cylindrical transparent member is provided inside openings of the fluorescent body and the fluorescence cutoff filter.

37. An illumination light application structure according to claim 28, wherein a light-blocking member is provided inside an opening of the fluorescent body.

38. An illumination light application structure according to claim 28, wherein a cylindrical transparent member is provided inside an opening of the fluorescent body.

39. An illumination light application structure according to claim 28, wherein an image transmitting optical system including one of a relay lens, an image fiber, and a SELFOC lens is provided on an image side of the objective optical system.

40. An illumination light application structure according to claim 39, wherein the image transmitting optical system is constructed with the SELFOC lens and the irradiation means includes an illumination optical system having an optical axis inclined with respect to an optical axis of the SELFOC lens so that excitation light emitted from the light source is obliquely incident on an entrance surface of the SELFOC lens.

41. An illumination light application structure according to claim 39, wherein the image transmitting optical system is constructed with a SELFOC lens and the SELFOC lens is provided with a low-refractive-index cladding layer on a periphery thereof.

42. An illumination light application structure according to claim 28, wherein the irradiation means includes chromatic aberration producing means placed on an optical path between the fluorescent body and the light source so that the fluorescent body is irradiated with excitation light through an optical path different from optical paths of light of wavelengths other than the excitation light due to a color error action and the light source placed to lie around the objective optical system.

43. An illumination light application structure according to claim 42, wherein the chromatic aberration producing means includes a cemented lens or a diffraction grating.

44. An illumination light application structure according to claim 28, further comprising a fluorescence cutoff filter configured into a size that is smaller in inside diameter than the fluorescent body and is practically identical in outside diameter with the fluorescent body proximate to a position of the entrance pupil of the objective optical system and having properties of transmitting excitation light and blocking fluorescent light emanating from the fluorescent body; a transparent member configured into an annular shape that has inside and outside diameters practically identical in size with the fluorescent body, provided between the fluorescent body and the fluorescence cutoff filter; and a concave lens and a convex lens arranged in this order from an object side inside the transparent member.

45. An illumination light application structure according to claim 28, wherein the observation optical apparatus is an endoscope.

46. An illumination light application structure according to claim 28, wherein the light source includes an LD or LED.

47. An endoscope provided with the illumination light application structure according to claim 28.

48. An illumination light application structure for irradiating an observation object with illumination light in an observation optical apparatus provided with an objective optical system inside a lens barrel whose top is configured into a slender shape, the illumination light application structure comprising:
    an annular scattering body located proximate to a position of an entrance pupil of the objective optical system, having a size that an inside diameter is larger than a diameter of the entrance pupil of the objective optical system and an outside diameter is practically identical with a diameter of a lens of a largest diameter in the objective optical system;
    a light source; and
    irradiation means irradiating the scattering body with light emitted from the light source through the objective optical system.

49. An illumination light application structure according to claim 48, wherein the irradiation means is provided with a reflecting mirror obliquely placed proximate to a position of a pupil conjugate with the entrance pupil of the objective optical system, including a reflecting surface having a diameter practically identical with a diameter of the pupil conjugate with the entrance pupil of the objective optical system in a state where the reflecting mirror is obliquely placed and is constructed so that the scattering body is irradiated with light passing through a periphery of the reflecting mirror, of the light emitted from the light source, through the objective optical system.

50. An illumination light application structure according to claim 48, wherein the irradiation means is constructed so that a plurality of light sources are annularly arranged with respect to an optical axis of the objective optical system and individual light emitted from the plurality of light sources passes through a periphery of a pupil conjugate with the entrance pupil of the objective optical system.

51. An illumination light application structure according to claim 48, wherein the irradiation means is constructed with a wavelength selective member having properties of reflecting the light emitted from the light source and transmitting light of remaining wavelengths, obliquely placed proximate to a position of a pupil conjugate with the entrance pupil of the objective optical system so as to reflect the light from the light source toward an objective optical system side.

52. An illumination light application structure according to claim 51, wherein the image transmitting optical system is constructed with a SELFOC lens and the SELFOC lens is provided with a low-refractive-index cladding layer on a periphery thereof.

53. An illumination light application structure according to claim 48, wherein an image transmitting optical system including one of a relay lens, an image fiber, and a SELFOC lens is provided on an image side of the objective optical system.

54. An illumination light application structure according to claim 53, wherein the image transmitting optical system is constructed with the SELFOC lens and the irradiation means includes an illumination optical system having an optical axis inclined with respect to an optical axis of the SELFOC lens so that excitation light emitted from the light source is obliquely incident on an entrance surface of the SELFOC lens.

55. An illumination light application structure according to claim 53, wherein the irradiation means includes chromatic aberration producing means placed on an optical path between the scattering body and the light source so that the scattering body is irradiated with light of preset wavelength through an optical path different from optical paths of light of wavelengths other than the light of the preset wavelength due to a color error action and the light source placed to lie around the objective optical system.

56. An illumination light application structure according to claim 55, wherein the chromatic aberration producing means includes a cemented lens or a diffraction grating.

57. An illumination light application structure according to claim 48, wherein the irradiation means includes chromatic aberration producing means placed on an optical path between the scattering body and the light source so that the scattering body is irradiated with light of preset wavelength through an optical path different from optical paths of light of wavelengths other than the light of the preset wavelength due to a color error action and the light source placed to lie around the objective optical system.

58. An illumination light application structure according to claim 57, wherein the chromatic aberration producing means includes a cemented lens or a diffraction grating.

59. An illumination light application structure according to claim 48, wherein the observation optical apparatus is an endoscope.

60. An illumination light application structure according to claim 48, wherein the light source is an LD or LED.

61. An endoscope provided with the illumination light application structure according to claim 48.

* * * * *